（12）United States Patent
Weikart et al.

(10) Patent No.: US 10,780,021 B2
(45) Date of Patent: Sep. 22, 2020

(54) CYCLOOLEFIN POLYMER CONTAINER WITH A SCRATCH RESISTANT AND ANTI-STATIC COATING

(71) Applicant: SIO2 MEDICAL PRODUCTS, INC., Auburn, AL (US)

(72) Inventors: Christopher Weikart, Auburn, AL (US); Ralf Kibele, Bruckmuehl (DE)

(73) Assignee: SIO2 MEDICAL PRODUCTS, INC., Auburn, AL (US)

( * ) Notice: Subject to any disclaimer, the term of this patent is extended or adjusted under 35 U.S.C. 154(b) by 273 days.

(21) Appl. No.: 15/552,989

(22) PCT Filed: Feb. 26, 2016

(86) PCT No.: PCT/US2016/019901
§ 371 (c)(1),
(2) Date: Aug. 23, 2017

(87) PCT Pub. No.: WO2016/138455
PCT Pub. Date: Sep. 1, 2016

(65) Prior Publication Data
US 2018/0049945 A1 Feb. 22, 2018

Related U.S. Application Data

(60) Provisional application No. 62/120,975, filed on Feb. 26, 2015, provisional application No. 62/198,286, filed on Jul. 29, 2015.

(51) Int. Cl.
*A61J 1/06* (2006.01)
*A61M 5/178* (2006.01)
*A61J 3/00* (2006.01)
*A61M 5/31* (2006.01)
*C09D 145/00* (2006.01)
(Continued)

(52) U.S. Cl.
CPC .............. *A61J 1/065* (2013.01); *A61J 3/002* (2013.01); *A61M 5/178* (2013.01); *A61M 5/3129* (2013.01); *C09D 145/00* (2013.01); *A61J 1/1425* (2015.05); *A61M 2205/0233* (2013.01);
(Continued)

(58) Field of Classification Search
CPC .......... A61J 1/065; A61J 3/002; A61J 1/1425; A61M 5/178; A61M 5/3129; A61M 2205/0233; A61M 2205/0238; C09D 145/00; C08F 32/04; G01N 23/2273
See application file for complete search history.

(56) References Cited

U.S. PATENT DOCUMENTS 2,008,217 A   7/1935   Matravers
5,298,587 A   3/1994   Hu et al.
(Continued)

FOREIGN PATENT DOCUMENTS

DE     4303570 C2    3/1997
DE     69421975 T2   3/2000
(Continued)

*Primary Examiner* — Michael C Miggins
(74) *Attorney, Agent, or Firm* — David B. Gornish

(57) ABSTRACT

Cycloolefin polymer (COP) containers, including vials or syringes, having a scratch-resistant and anti-static coating on the external wall results in a reduction or prevention of static charge on the articles. The combination of an anti-scratch and anti-static coating results in the reduction of the attraction of charged particles to the container, leading to decreased particulate contamination while providing scratch resistance.

36 Claims, 7 Drawing Sheets

(51) Int. Cl.
    *A61J 1/14*          (2006.01)
    *C08F 32/04*       (2006.01)
    *G01N 23/2273*   (2018.01)

(52) U.S. Cl.
    CPC ...... *A61M 2205/0238* (2013.01); *C08F 32/04* (2013.01); *G01N 23/2273* (2013.01)

(56) References Cited

U.S. PATENT DOCUMENTS

| | | |
|---|---|---|
| 7,985,188 B2 | 7/2011 | Felts et al. |
| 8,435,605 B2 | 5/2013 | Aitken et al. |
| 2011/0311584 A1 | 12/2011 | Sahin et al. |
| 2012/0159643 A1 | 6/2012 | Bradley et al. |
| 2012/0195917 A1 | 8/2012 | Sahin et al. |
| 2013/0071138 A1 | 3/2013 | Goto |
| 2013/0143683 A1 | 6/2013 | Solhaug |
| 2014/0030808 A1 | 1/2014 | Sahin et al. |
| 2014/0178438 A1 | 6/2014 | Sahin et al. |
| 2014/0251859 A1 | 9/2014 | Weikart et al. |
| 2015/0086612 A1 | 3/2015 | Sahin et al. |

FOREIGN PATENT DOCUMENTS

| | | |
|---|---|---|
| DE | 69911381 T2 | 6/2004 |
| EP | 0610831 A2 | 8/1994 |
| WO | 2012/072096 A1 | 6/2012 |
| WO | 2014/072061 A1 | 5/2014 |
| WO | 2014/075697 A1 | 5/2014 |
| WO | 2014/075788 A1 | 5/2014 |
| WO | 2014/082729 A1 | 6/2014 |
| WO | 2014/164928 A1 | 10/2014 |

CYCLOOLEFIN POLYMER CONTAINER WITH A SCRATCH RESISTANT AND ANTI-STATIC COATING

CROSS-REFERENCE TO RELATED APPLICATIONS

This application is a U.S. National Phase of International Application No. PCT/US2016/019901 filed Feb. 6, 2016, which claims priority to U.S. Provisional Patent Application Nos. 62/120,975, filed Feb. 26, 2015 and 62/198,286, filed Jul. 29, 2015, which are incorporated herein by reference in their entirety.

This application claims the priority of each of the following patent applications: U.S. Ser. No. 62/120,975, filed 26 Feb. 2015, and U.S. Ser. No. 62/198,286, filed 29 Jul. 2015. The entire disclosure of each of these prior applications is incorporated by reference here for all purposes, including for continuity of disclosure.

FIELD OF THE INVENTION

The invention relates to cycloolefin polymer (COP) containers, including vials or syringes, having a scratch-resistant and anti-static build-up coating. The invention generally relates to anti-scratch and anti-static coatings for plastic articles, e.g., containers, to reduce or prevent static charge on the articles. More particularly, the invention relates to coatings on plastic containers to reduce attraction of charged particles to the container, in order to decrease particulate contamination while providing scratch resistance.

BACKGROUND

An important consideration in manufacturing packaging or containers for regulated products, e.g., pharmaceuticals, is to ensure that the pharmaceutical product to be contained within a container is substantially free of contaminants. Therefore, processes for manufacturing and filling pharmaceutical containers with product, are typically performed under cleanroom conditions. One cause of potential contamination is particulates. Particulate contamination can originate from various sources, which may be generally divided into two categories: (1) intrinsic contaminants; and (2) extrinsic contaminants. Intrinsic contaminants are product and process related particulates, for example, laser etching residues, filter media, cleanroom uniform fibers, rubber and plastic particles from filter housing, and needle shields. Extrinsic contamination comes from sources unrelated to product or process, for example, hair, skin cells, pollen, clothing fibers, salt and soil. While filtration systems and good manufacturing practices can limit the surface and airborne particulate count in an area where containers are being manufactured or filled, these things do not always reduce particulate count on the container surfaces to acceptable levels. One particular challenge is presented by static charges of manufactured plastic containers, which tend to attract charged particles. Even if the airborne/surface particulate count is relatively low, a plastic container with a strong static charge can act as a magnet of sorts to attract particulate contaminants and cause them to adhere to the container.

COP articles that are within the scope of the present invention include, for example, laboratory ware (e.g., tubes and vials) and parenteral containers (e.g., syringes and cartridges).

Containers made of plastics have an advantage over glass containers of being low in weight and having a high degree of break resistance. A disadvantage of plastics containers is, however, their high susceptibility to scratching.

Plastics containers or vials or syringes are frequently used for pharmaceutical preparations. For the production of the preparations, the plastics containers are often sterilized together with the pharmaceutical preparation. Commercially available plastics containers contain polyethylene propylene (PEP) or polypropylene (PP) and cannot be autoclaved, but must be radiation-sterilized or sterilized with ethylene oxide.

In addition, PEP and PP plastic containers have the additional disadvantage that they are milky and for that reason visual inspection of the contents of the container is not possible.

COP (cycloolefin polymer) is a highly pure, clear, sterilizable resin with excellent moisture barrier properties; this makes it an excellent alternative to glass in a wide range of medical products. While a container made of cycloolefin polymer COP is clear, it is also susceptible to scratching and static build-up.

Previously, the problems of scratching and status build-up have been addressed by providing separate coatings or treatments for each problem. The two types of functionality have not been compatible in a single coating or other treatment, thus complicating the manufacture of a container satisfying both needs.

SUMMARY

An aspect of the invention is a container comprising a wall made of a cycloolefin polymer, for example cyclic olefin polymer (COP), having an internal surface enclosing a lumen, an external contact surface, and an external coating on the contact surface comprising an anti-scratch agent and an anti-static agent. The anti-scratch agent and anti-static agent optionally are constituents of a homogeneously blended external coating or anti-static and anti-scratch coating. Other aspects and features of the invention will be apparent from the description and claims that follow.

BRIEF DESCRIPTION OF DRAWING FIGURES

Figure 13:
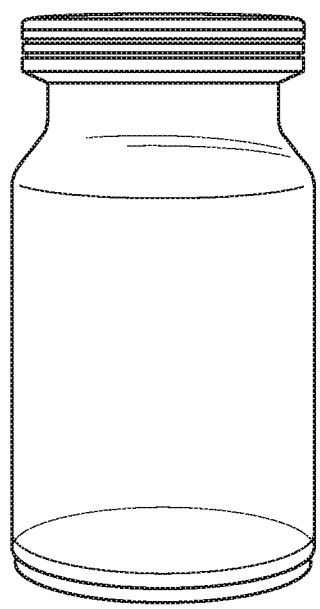

FIG. 13 is a perspective view drawn from a photograph of a COP vial according to the invention as tested in Examples 3-8, having an anti-static and anti-scratch coating according to the present invention with a static load of less than 0.5 kV, preferably essentially no static load, most preferably a static load of 0 kV after receiving an electrostatic charge and being held for 60 minutes, which did not attract cigarette ash, usable according to any embodiment of the invention.

Figure 14:
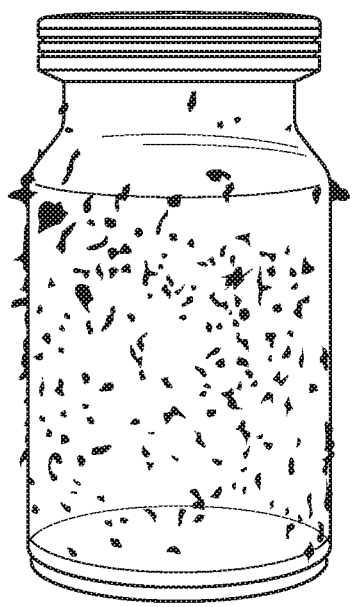

FIG. 14 is a perspective view drawn from a photograph of a COP vial control as tested in Examples 3-8, not coated according to the present invention, with a static load of more than 0.5 kV, optionally a static load of 1 kV after receiving an electrostatic charge and being held for 60 minutes, which attracted cigarette ash and thus is more subject to particulate contamination than the vial of FIG. 13.

The following reference characters are used in the description and drawings.

| Ref. Char. | |
|---|---|
| 10 | Syringe |
| 12 | Parenteral container |
| 12a | Container |
| 12b | Container |
| 12c | Container |
| 14 | Barrel |
| 16 | Internal surface |
| 18 | Lumen |
| 20 | Needle |
| 22 | Proximal opening (of 20) |
| 24 | (Distal) opening (of 20) |
| 26 | external coating or anti-static and anti-scratch coating(s) |
| 26a | Contact surface |
| 28 | Needle shield |
| 30 | Tie coating |
| 32 | Opening |
| 34 | Barrier coating |
| 36 | Crimp |
| 38 | Plunger rod |
| 40 | Fluid material |
| 42 | External sliding surface (of 36) |
| 44 | Base surface |
| 46 | Container processing line |
| 47 | Surface (of 46) |
| 48 | Interface |
| 50 | Bumper |
| 51 | Generally cylindrical surface |
| 52 | Generally cylindrical wall |
| 54 | Closure |
| 56 | Top Flange |
| 58 | Radial enlargement (of 56) |
| 62 | Static dissipation bar, 0 sec. |
| 64 | Static dissipation bar, 10 sec. |
| 66 | Static dissipation bar, 0 sec. |
| 68 | Static dissipation bar, 10 sec. |
| 70 | Static dissipation bar, 0 sec. |
| 72 | Static dissipation bar, 10 sec. |
| 74 | Static dissipation bar, 0 sec. |
| 76 | Static dissipation bar, 10 sec. |
| 78 | Static charge plot, uncoated COP |
| 80 | Static charge plot, coated COP |

DETAILED DESCRIPTION OF THE PREFERRED EMBODIMENTS

Figure 7:
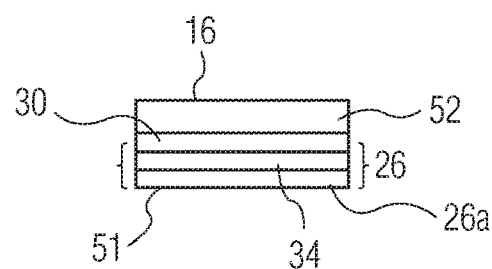
FIG. 7 is a detail view of one embodiment of the wall and external coating set of the vessel shown in FIG. 6, usable with any embodiment of the invention.
Figure 8:
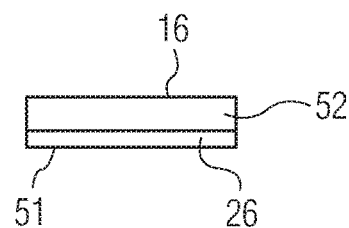
FIG. 8 is a detail view of another embodiment of the wall and external coating set of the vessel shown in FIG. 6, usable with any embodiment of the invention.

Referring now to FIGS. 1-10, a parenteral container, for example 12, 12a, 12b, or 12c, or a prefilled syringe 10, for containing or storing a pharmaceutical or diagnostic fluid or other material 40 or other contents incorporates an optionally clear, optionally transparent coating or other mar inhibiting contact surface or external coating or anti-static and anti-scratch coating set 26, which can be a single coating 26 as shown in FIG. 8 or a coating set 26 including as one or more layers an anti-static and anti-scratch coating 26a as shown in FIG. 7, typically on the exterior surface of the parenteral container 12, 12a, 12b, or 12c (although if the processing equipment touches the interior of the plastic container a mar inhibiting contact surface 26 optionally can be provided within the containers 12, 12a, 12b, or 12c). The mar inhibiting contact surface or external coating or anti-static and anti-scratch coating 26 enables the container to be more resistant to mars than an uncoated container.

Optionally in any embodiment, the containers 12, 12a, 12b, or 12c can be made of thermoplastic base material. As another option in any embodiment, the containers 12, 12a, 12b, or 12c can be made of glass base material. Although glass is less subject to marring than plastic, the present development may still find utility for processing glass vessels.

Optionally in any embodiment, the coating set 26 can be transparent. Optionally in any embodiment the coating set 26 enables the parenteral container 12, 12a, 12b, or 12c to run through traditional glass vial filling lines such as the container processing line 46, optionally without modifications. Optionally in any embodiment the coating set 26 does not contain extractables that are harmful to the pharmaceutical or diagnostic fluid or other material 40 packaged in the parenteral containers 12, 12a, 12b, or 12c.

Optionally in any embodiment the coating set 26 can be applied quickly, easily, and inexpensively. Optionally in any embodiment, filling and other processing of the parenteral containers 12, 12a, 12b, or 12c can be scaled up in a high volume manufacturing process.

Figure 1:
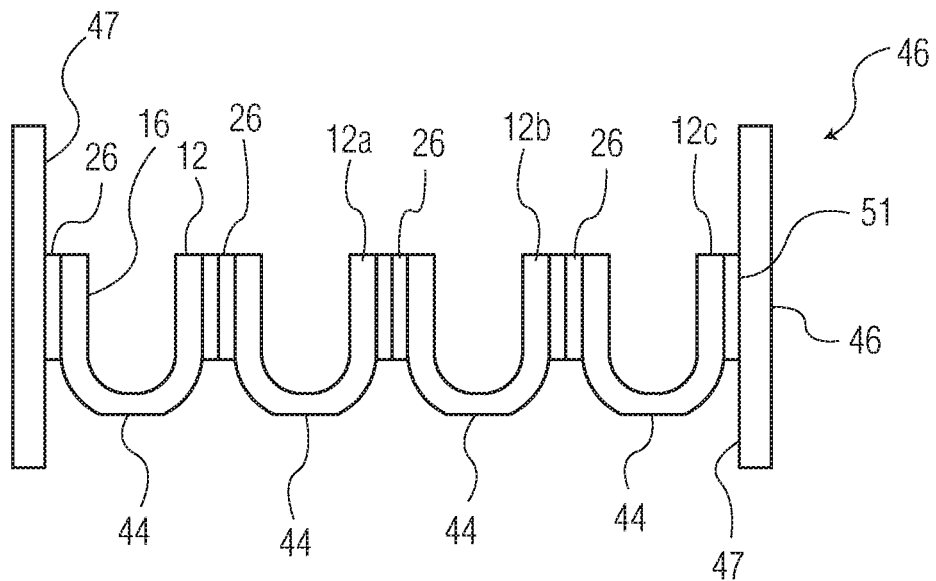
FIG. 1 is a schematic sectional view of several unfilled parenteral containers in contact with each other and with processing equipment surfaces, usable with any embodiment of the invention.
Figure 2:
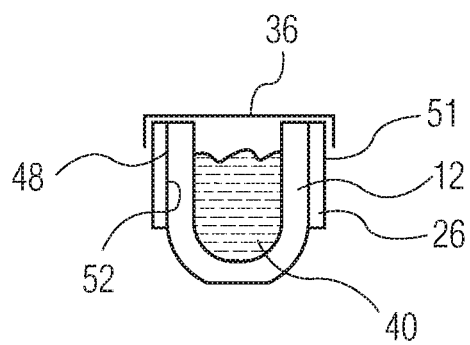
FIG. 2 is a view similar to FIG. 1 of a filled and capped parenteral container, usable with any embodiment of the invention.

Referring to FIGS. 1 and 2, a method of packaging pharmaceutical or diagnostic fluid or other material 40 in thermoplastic parenteral containers 12, 12a, 12b, or 12c is illustrated schematically. Generally speaking, the method includes providing multiple thermoplastic base material parenteral containers 12, 12a, 12b, or 12c. A mar inhibiting contact surface or external coating or anti-static and anti-scratch coating 26 is provided on each container 12, 12a, 12b, or 12c. The mar inhibiting contact surface or external coating or anti-static and anti-scratch coating 26 on a container 12, 12a, 12b, or 12c optionally can be brought in contact with one or more of the multiple parenteral containers 12, 12a, 12b, or 12c or a processing equipment surface 47, or both. Optionally in any embodiment, the mar inhibiting contact surfaces of contacting containers 12, 12a, 12b, or 12c come directly into contact with each other, although as another option contact can occur between a mar inhibiting contact surface of one container and a surface of another container that is not mar resistant. Before, during, or after any such contact, or at more than one of these stages, the multiple parenteral containers 12, 12a, 12b, or 12c can be filled with a pharmaceutical or diagnostic fluid or other material 40.

Optionally in any embodiment, the mar inhibiting contact surface or external coating or anti-static and anti-scratch coating 26 comprises a coating provided on a container 12, 12*a*, 12*b*, or 12*c*. As another option in any embodiment, the mar inhibiting contact surface or external coating or anti-static and anti-scratch coating 26 comprises a surface of the thermoplastic base material. Thus, although the Figures show an interface 48 between the base material and the mar resistant contact surface or external coating or anti-static and anti-scratch coating 26, the material on both sides of the interface can be the same as well as different, and the base material and the mar resistant contact surface or external coating or anti-static and anti-scratch coating 26 optionally can be formed as one continuous part, with no interface between them.

Optionally in any embodiment, the mar inhibiting contact surface or external coating or anti-static and anti-scratch coating 26 can be an exterior surface of the container 12, 12*a*, 12*b*, or 12*c*. Optionally in any embodiment, the mar inhibiting contact surface or external coating or anti-static and anti-scratch coating 26 can be an interior surface 16 of the container 12, 12*a*, 12*b*, or 12*c*. Optionally in any embodiment, the mar inhibiting contact surface or external coating or anti-static and anti-scratch coating 26 optionally can be a generally cylindrical surface 51 of the container 12, 12*a*, 12*b*, or 12*c*. Alternatively in any embodiment, the mar inhibiting contact surface can be a base surface 44 of the container 12, 12*a*, 12*b*, or 12*c* on which the container 12, 12*a*, 12*b*, or 12*c* normally stands. Alternatively in any embodiment, the mar inhibiting contact surface or external coating or anti-static and anti-scratch coating 26 optionally can be a side wall, optionally a generally cylindrical wall, 52 of the container 12, 12*a*, 12*b*, or 12*c*.

Optionally in any embodiment, the mar inhibiting contact surface or external coating or anti-static and anti-scratch coating 26 can be provided after the parenteral container 12, 12*a*, 12*b*, or 12*c* is formed. Optionally in any embodiment, the mar inhibiting contact surface or external coating or anti-static and anti-scratch coating 26 can be provided before contact is made between two of the parenteral containers 12, 12*a*, 12*b*, or 12*c*. Optionally in any embodiment, the mar inhibiting contact surface or external coating or anti-static and anti-scratch coating 26 can be provided on a parenteral container 12, 12*a*, 12*b*, or 12*c* after the parenteral container 12, 12*a*, 12*b*, or 12*c* is formed and before the parenteral container 12, 12*a*, 12*b*, or 12*c* contacts a processing equipment surface 47.

Optionally in any embodiment, the thermoplastic parenteral containers 12, 12*a*, 12*b*, or 12*c* are vials. Alternatively in any embodiment, the thermoplastic parenteral containers 12, 12*a*, 12*b*, or 12*c* are cartridges. Alternatively in any embodiment, the thermoplastic parenteral containers 12, 12*a*, 12*b*, or 12*c* are syringes. Alternatively in any embodiment, the thermoplastic parenteral containers 12, 12*a*, 12*b*, or 12*c* are containers of two or more different kinds, such as a syringe and a cartridge, a syringe and a vial, or a cartridge and a vial.

Optionally in any embodiment, the mar inhibiting contact surface or external coating or anti-static and anti-scratch coating 26*a* or coating set 26 can comprise a polysiloxane coating. The mar inhibiting contact surface or external coating or anti-static and anti-scratch coating set 26 optionally can comprise a barrier coating 34, for example an $SiO_x$ coating, in which x optionally can be from about 1.5 to about 2.9. The mar inhibiting contact surface or external coating or anti-static and anti-scratch coating set 26 optionally can comprise an $SiO_xC_y$ or $SiN_xC_y$ tie coating 30, in which x optionally can be from about 0.5 to about 2.4 and y optionally can be from about 0.6 to about 3, each as determined by XPS analysis. As is well known, XPS analysis detects silicon, oxygen, carbon, and nitrogen but does not detect hydrogen.

Optionally in any embodiment, the mar inhibiting contact surface or external coating or anti-static and anti-scratch coating 26 comprises a plasma enhanced chemical vapor deposition tie coating 30 comprising silicon, oxygen, and carbon in an atomic ratio of 1 part silicon, from 0.5 to 2.4 parts of oxygen, and from 0.6 to 3 parts carbon, as determined by XPS analysis.

Optionally in any embodiment, the tie coating further comprises hydrogen and the atomic ratio optionally can be 1 part silicon, from 0.5 to 2.4 parts of oxygen, from 0.6 to 3 parts carbon, and from 2 to 12 parts of hydrogen, as determined by Rutherford back-scattering analysis, which detects silicon, oxygen, carbon, and hydrogen.

Optionally in any embodiment, the mar inhibiting contact surface comprises a plasma enhanced chemical vapor deposition tie coating 30 comprising silicon, nitrogen, and carbon in an atomic ratio of 1 part silicon, from 0.5 to 2.4 parts of nitrogen, and from 0.6 to 3 parts carbon, as determined by XPS analysis. Optionally the coating further comprises hydrogen and the atomic ratio is 1 part silicon, from 0.5 to 2.4 parts of nitrogen, from 0.6 to 3 parts carbon, and from 2 to 12 parts of hydrogen, as determined by Rutherford back-scattering analysis.

Optionally in any embodiment, the mar inhibiting contact surface or external coating or anti-static and anti-scratch coating 26 comprises a silicon nitride coating, alternatively an amorphous carbon coating, alternatively a perfluorinated hydrocarbon coating. Optionally in any embodiment, the mar inhibiting contact surface or external coating or anti-static and anti-scratch coating 26 comprises a Diamond-Shield® coating as available from Morgan Advanced Ceramics, Inc., Hayward Calif. Optionally in any embodiment, the mar inhibiting contact surface or external coating or anti-static and anti-scratch coating 26 comprises a diamond-like carbon (DLC) coating.

Optionally in any embodiment, the mar inhibiting contact surface or external coating or anti-static and anti-scratch coating 26 comprises a polyvinylidene chloride (PVdC) coating as disclosed by U.S. Pat. No. 7,985,188.

Optionally in any embodiment, the mar inhibiting contact surface or external coating or anti-static and anti-scratch coating 26 comprises a sol-gel coating. Examples of suitable sol-gel coatings include a silica filled nanocomposite coating, an ORMOCER® anti-scratch coating available from Fraunhofer Institute, Munich Germany, or a biaxially oriented PLA-Montmorillonite-Nanocomposite available from VTT Technical Research Centre of Finland.

Optionally in any embodiment, the mar inhibiting contact surface or external coating or anti-static and anti-scratch coating 26 comprises an acrylic coating, for example a Urethane Acrylate coating. Desmolux® urethane acrylate coating, available from Bayer Aktiengesellschaft, Leverkusen Germany, can be used, for example.

Optionally in any embodiment, the mar inhibiting contact surface or external coating or anti-static and anti-scratch coating 26 comprises a water borne coating system. The mar inhibiting contact surface or external coating or anti-static and anti-scratch coating 26 optionally can comprise a Nano-myte® Optical coating as available from NEI Corporation, Somerset N.J. The mar inhibiting contact surface or external coating or anti-static and anti-scratch coating 26 optionally can comprise a silane derived acrylic polyol coating, available from Dow Corning Corporation, Midland, Mich. The mar inhibiting contact surface or external coating or antistatic and anti-scratch coating 26 optionally can comprise a pre-hydrolyzed and pre-condensed silane coating including specifically designed catalyst systems, available from Dow Corning Corporation, Midland, Mich.

The mar inhibiting contact surface or external coating or anti-static and anti-scratch coating 26 optionally can comprise a silane coating terminated with OH, glycol or heavy alcohol groups.

The mar inhibiting contact surface or external coating or anti-static and anti-scratch coating 26 optionally can comprise an epoxy coating. The mar inhibiting contact surface or external coating or anti-static and anti-scratch coating 26 optionally can comprise a Scotchkote® abrasion resistant epoxy or polyurethane coating available from 3M Company, St. Paul, Minn.

The mar inhibiting contact surface or external coating or anti-static and anti-scratch coating 26 optionally can comprise a polysiloxane resin coating. For example, the mar inhibiting contact surface or external coating or anti-static and anti-scratch coating 26 optionally can comprise a Duravue® abrasion resistant polysiloxane hardcoat, available from T.S. Polymers, Inc., Batavia, Ohio (see http://www.tspinc.com/anti-scratch-coatings).

The mar inhibiting contact surface or external coating or anti-static and anti-scratch coating 26 optionally can comprise a Parylene® coating, for example of Parylene® HTx. Such coatings and other useful coatings are described in PCT/US13/62247, filed 27 Sep. 2013, by SiO$_2$ Medical Products, Inc. and incorporated here by reference.

Optionally in any embodiment, the mar inhibiting contact surface or external coating or anti-static and anti-scratch coating 26 can be provided by modifying the formulation of a bulk thermoplastic composition of one or more of the parenteral containers 12, 12a, 12b, or 12c to add an slip agent. A slip agent provides surface lubrication to the polymer during and after formation of the parenteral containers 12, 12a, 12b, or 12c. The slip agents contemplated include amides of fatty acids, for example long-chain fatty acid amides, in which the fatty acid chains have from 18 to 22 carbon atoms and preferably a single site of unsaturation, like oleyl ($C_{18}$, single unsaturated).

In any embodiment, the mar inhibiting contact surface or external coating or anti-static and anti-scratch coating 26 optionally can comprise a transparent coating. The coated surface optionally can be indistinguishable by the unaided human eye from the corresponding uncoated surfaces.

Optionally in any embodiment, the mar inhibiting contact surface of the container 12, 12a, 12b, or 12c can be effective to reduce marring resulting from bringing the container 12, 12a, 12b, or 12c into contact with other parenteral containers 12, 12a, 12b, or 12c or processing equipment surfaces 47 in an automated container processing line 46.

In any embodiment, the mar inhibiting contact surface or external coating or anti-static and anti-scratch coating 26 of the container 12, 12a, 12b, or 12c optionally can be effective to reduce marring resulting from processing the containers 12, 12a, 12b, or 12c in equipment used, or specified and configured for use, in glass container filling or other processing lines, optionally without modifications. Alternatively, simpler, less expensive, or fewer modifications can be made to equipment used for glass container filling lines, using the present invention, than if a mar inhibiting contact surface or external coating or anti-static and anti-scratch coating 26 was not provided on the containers 12, 12a, 12b, or 12c.

In any embodiment, the mar inhibiting contact surface or external coating or anti-static and anti-scratch coating 26 optionally can be at least essentially free of extractables that are prohibited in the drug product. Alternatively, the mar inhibiting contact surface or external coating or anti-static and anti-scratch coating 26 optionally can be free of any extractables in an amount harmful to the drug product.

In any embodiment, the mar inhibiting contact surface or external coating or anti-static and anti-scratch coating 26 optionally reduces the coefficient of friction resulting from sliding motion between two mar inhibiting contact surfaces or external coating or anti-static and anti-scratch coatings 26 when in contact with each other. Optionally in any embodiment, the mar inhibiting contact surface or external coating or anti-static and anti-scratch coating 26 reduces the coefficient of friction resulting from sliding motion between a mar inhibiting contact surface or external coating or anti-static and anti-scratch coating 26 and an equipment surface 47 when in contact with each other. Optionally in any embodiment, the mar inhibiting contact surfaces 26 comprise coated surfaces, and the coated surfaces exhibit less sliding friction, with respect to the container bulk material, than the corresponding uncoated surfaces. Optionally in any embodiment, the coated surfaces exhibit less sliding friction, with respect to other mar inhibiting contact surfaces 26, than the corresponding uncoated surfaces. Optionally in any embodiment, the coated surfaces are harder than the corresponding uncoated surfaces.

Optionally in any embodiment, the mar inhibiting contact surfaces 26 reduce the incidence per processed container of at least one of the following types of mars—chips, cracks, abrasions, distortions, or adhered foreign material—compared to corresponding uncoated surfaces.

In any embodiment, the equipment surface 47 optionally can be made of stainless steel, alternatively nylon.

In any embodiment, the mar inhibiting contact surface or external coating or anti-static and anti-scratch coating 26 optionally can comprise a coating applied by vapor phase polymerization (VPP) coating technology—for example the technology disclosed by U.S. Pat. No. 5,374,483, issued to Dow Corning Corporation, Midland, Mich. Optionally in any embodiment, the mar inhibiting contact surface or external coating or anti-static and anti-scratch coating 26 can comprise a coating applied by chemical vapor deposition (CVD). Examples of chemical vapor deposition follow. The mar inhibiting contact surface or external coating or anti-static and anti-scratch coating 26 optionally can comprise a coating applied by plasma enhanced chemical vapor deposition (PECVD), for example by technology disclosed by U.S. Pat. No. 7,985,188, incorporated here by reference.

The mar inhibiting contact surface or external coating or anti-static and anti-scratch coating 26 optionally can comprise a coating applied by plasma impulse chemical vapor deposition (PICVD), for example by a process disclosed in U.S. Pat. No. 8,435,605, issued to Corning, Incorporated, Corning, N.Y., incorporated here by reference.

The mar inhibiting contact surface or external coating or anti-static and anti-scratch coating 26 optionally can comprise a coating applied by thermal chemical vapor deposition. Thermal chemical vapor deposition is disclosed for example in FIGS. 5 and 12 and the corresponding parts of the specification of PCT/US13/62247, filed 27 Sep. 2013, by SiO$_2$ Medical Products, Inc. and incorporated here by reference.

The mar inhibiting contact surface or external coating or anti-static and anti-scratch coating set 26 optionally can comprise a barrier coating 34 or a lubricity coating, each as described in U.S. Pat. No. 7,985,188, incorporated here by reference, or a combination of both. The mar inhibiting contact surface or external coating or anti-static and anti-scratch coating 26 optionally can comprise a pH protective coating, as described in WO2013/071138, filed by SiO$_2$ Medical Products, Inc. and incorporated here by reference.

The mar inhibiting contact surface or external coating or anti-static and anti-scratch coating 26 optionally can comprise an anti-abrasion coating of SiO$_x$C$_y$, as described in U.S. Pat. No. 5,298,587 of The Dow Chemical Co., incorporated by reference here.

In any embodiment, the mar inhibiting contact surface or external coating or anti-static and anti-scratch coating 26 optionally can be a coating applied by dipping, spraying, or both.

The mar inhibiting contact surface or external coating or anti-static and anti-scratch coating 26 optionally can be formed by incorporating an slip agent into the resin composition of the bulk container wall.

The mar inhibiting contact surface or external coating or anti-static and anti-scratch coating 26 optionally can be formed by molding bumpers 50 into the containers 12, 12*a*, 12*b*, or 12*c*.

Figure 3:
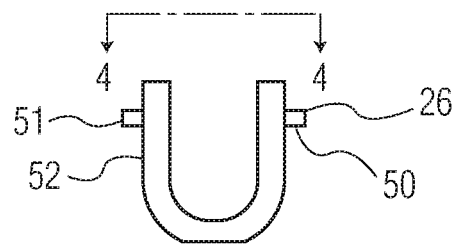
FIG. 3 is a view similar to FIG. 2 of a particular adaptation of a mar inhibiting control surface, usable with any embodiment of the invention.
Figure 4:
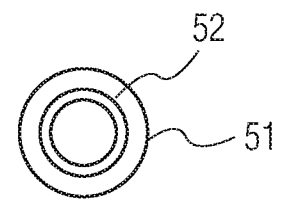
FIG. 4 is a top plan view taken from line 4-4 of FIG. 3.

Optionally in any embodiment, the container 12, 12*a*, 12*b*, or 12*c* has a generally cylindrical wall 52 and the bumper 50 optionally can be a rib molded into the generally cylindrical wall 52 of each container 12, 12*a*, 12*b*, or 12*c*, as shown for example in FIGS. 3 and 4. At least a portion of the rib or bumper 50 has a shape or surface finish configured for masking mars. For example it can be a frosted surface or a patterned surface. Optionally in any embodiment, as illustrated in FIG. 4, one or more ribs or bumpers 50 can extend circumferentially about the generally cylindrical surface 51.

Figure 5:
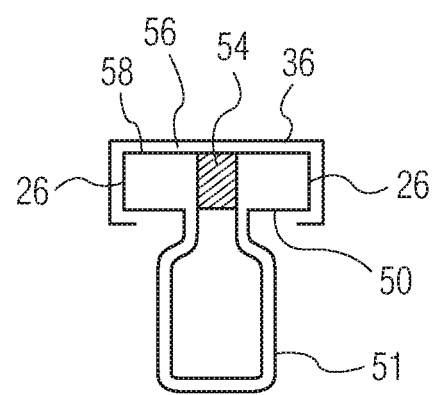
FIG. 5 is a view similar to FIG. 2 of a particular adaptation of a mar inhibiting control surface, usable with any embodiment of the invention.
Figure 6:
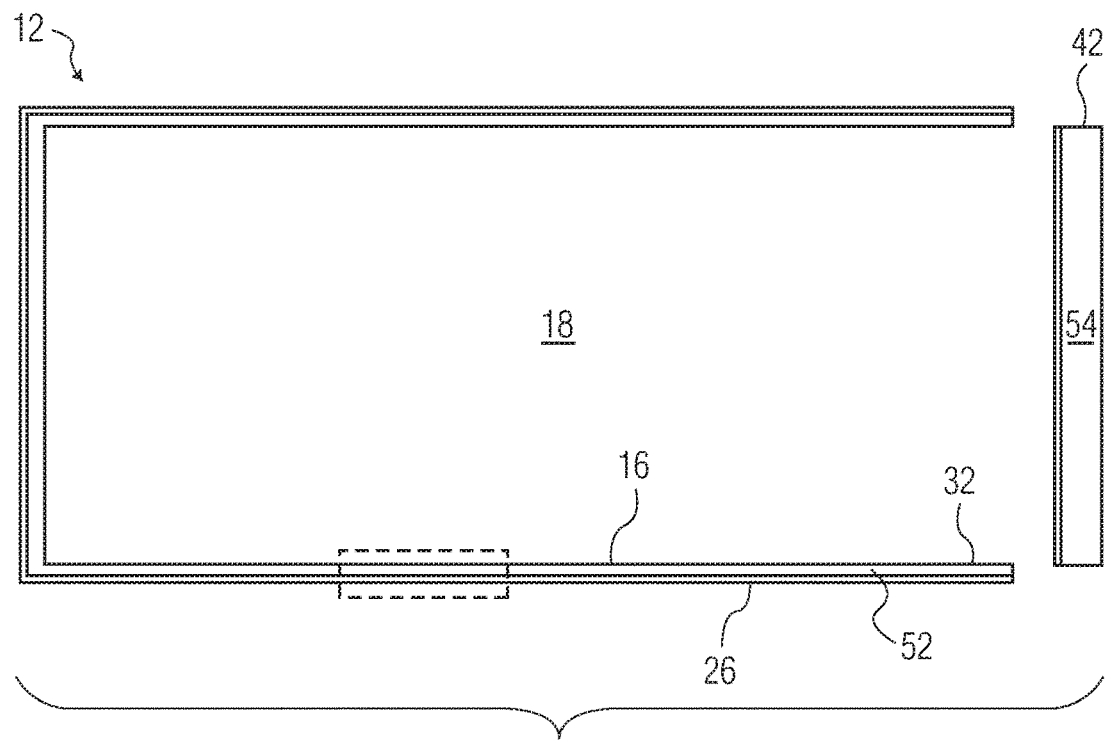
FIG. 6 is an exploded diagrammatic sectional view of a vessel and closure, for example but not limited to a parenteral container, a blood tube, a syringe, a cartridge, a vial, or an ampoule usable with any embodiment of the invention.
Figure 9:
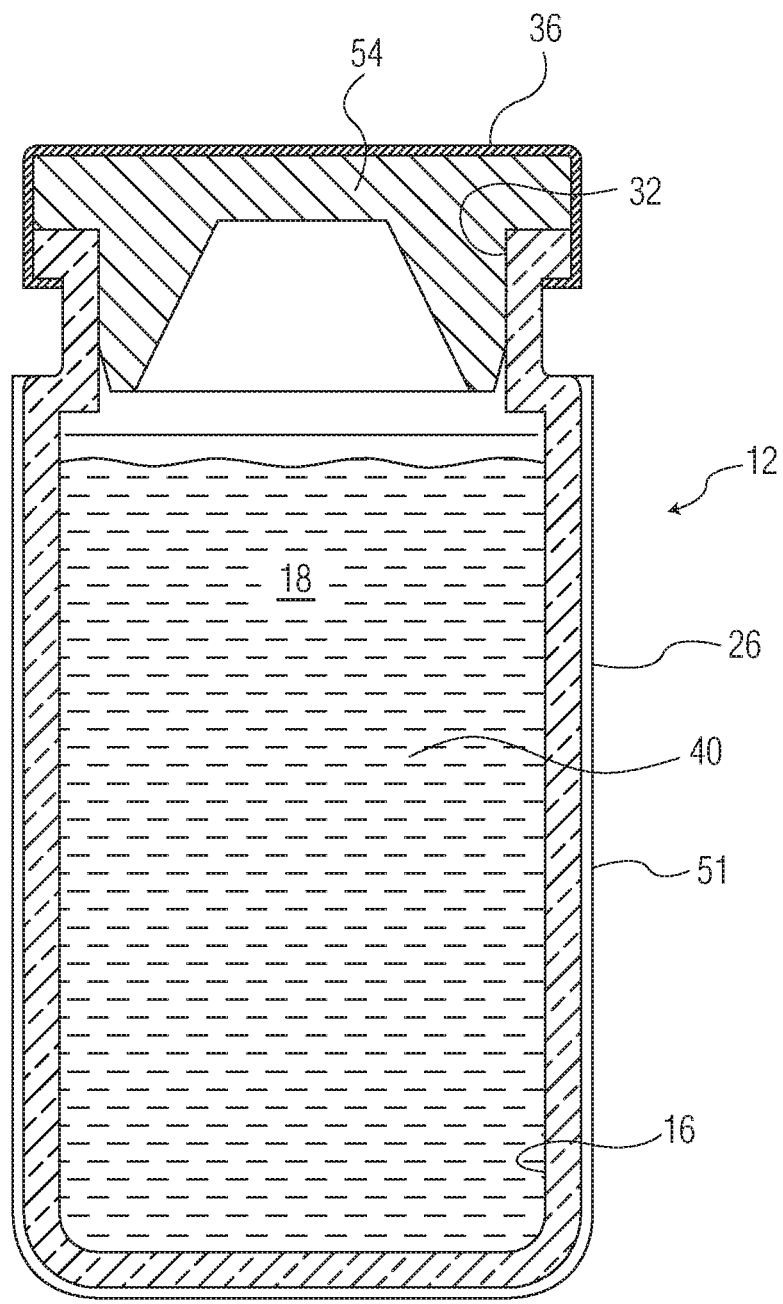
FIG. 9 is a diagrammatic view of the parenteral container of FIG. 6, more specifically configured as a filled vial, usable with any embodiment of the invention.
Figure 10:
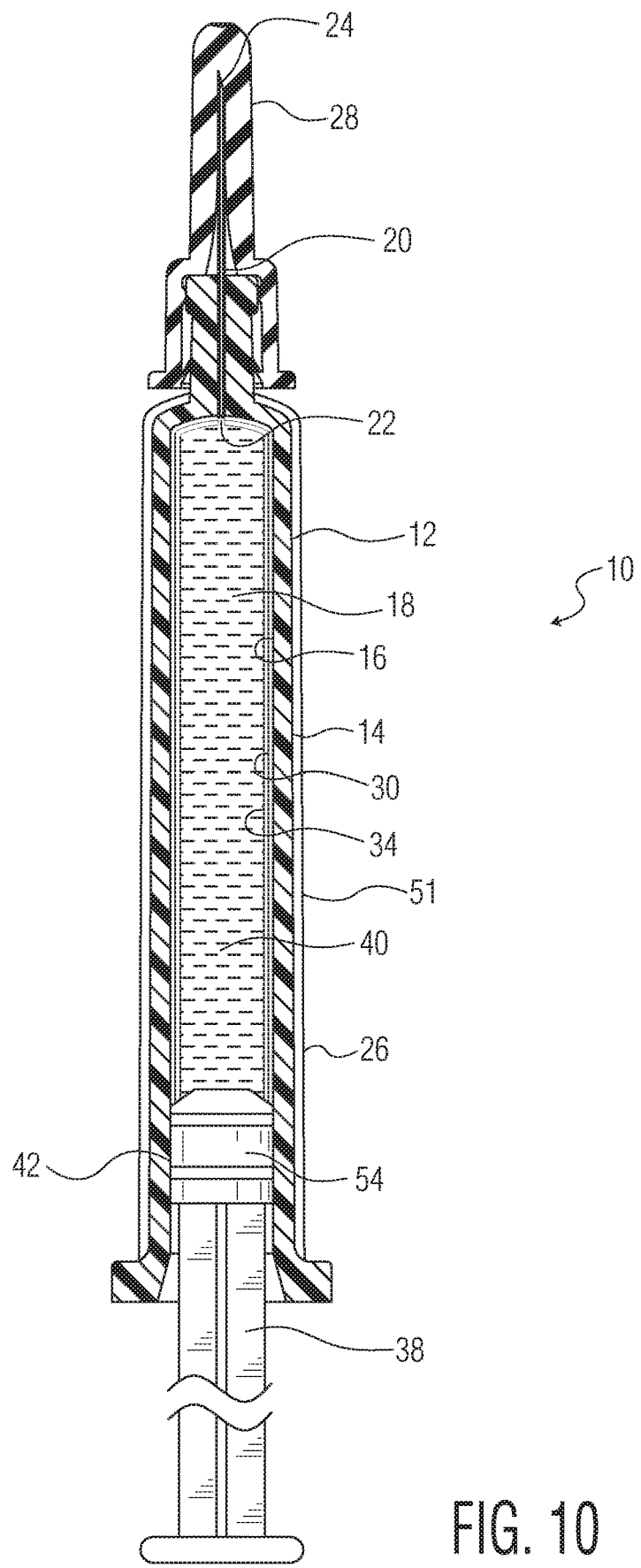
FIG. 10 is a diagrammatic view of the parenteral container of FIG. 6, more specifically configured as a prefilled syringe, usable with any embodiment of the invention.

Optionally in any embodiment, the container 12, 12*a*, 12*b*, or 12*c* can be a vial, as shown in FIG. 5, having a generally cylindrical wall 52 and an opening 32 adapted to receive a closure 54, which in the case of a parenteral container 12 embodied as a vial, as shown in FIGS. 5 and 9 can further comprise a crimp 36. The bumper 50 optionally can be a radial enlargement 58 of the top flange presenting a circumferential mar inhibiting contact surface or external coating or anti-static and anti-scratch coating 26 beyond the generally cylindrical wall 52 of each container 12, 12*a*, 12*b*, or 12*c*. The vial of any embodiment can be closed by placing a closure 54 on the container 12, 12*a*, 12*b*, or 12*c* configured to cover the circumferential mar inhibiting contact surface or external coating or anti-static and anti-scratch coating 26. The cap can thus hide any mars that are formed on the mar inhibiting contact surface or external coating or anti-static and anti-scratch coating 26. Using this option, the mar inhibiting contact surface or external coating or anti-static and anti-scratch coating 26 could be defined by the bulk material of the container 12, 12*a*, 12*b*, or 12*c*, and would be a mar concealing feature, as well as inhibiting mars of the generally cylindrical wall 52.

The processing equipment of the container processing line 46 used according to this disclosure can be the full range of such equipment known now or developed in the future. The following disclosure is merely exemplary of the full range of such equipment.

The processing equipment 46 of any embodiment optionally can comprise a thermoplastic surface 47, for example a nylon surface or a Teflon® polytetrafluoroethylene surface 47 contacted by mar inhibiting contact surfaces 26. The processing equipment 46 of any embodiment optionally can comprise a metallic surface 47, for example a stainless steel surface 47 contacted by mar inhibiting contact surfaces 26.

The processing equipment 46 contacted by mar inhibiting contact surfaces 26 optionally can comprise any one or any combination of the following types of equipment: a container feeder, a container guide, a container orienter, a container gripper, a container loader, a container conveyor, a container indexer, a container filler, a container capper, a container crimper, a container picker, a container placer, a container inspection station, a container coating station, a container labeler, a container cartoner, a conveyor belt, a table feeder, a rotary table feeder, a turntable, a rotary collecting wheel, a continuous feeder, a row by row loader, a scroll feeder, a screw feeder, a walking beam conveyor, a pick and place conveyor, a stoppering system, a crimper, a rotary crimping wheel, a transfer sleeve, a gating star wheel, a tub loader, a tub unloader, a tub unloading gripper, and/or a tub. This list of equipment is exemplary of all such equipment.

The parenteral container optionally has a mar inhibiting contact surface or external coating or anti-static and anti-scratch coating 26 and a non-mar inhibiting surface such as the generally cylindrical wall 52.

The base material used to form the parenteral containers 12, 12*a*, 12*b*, or 12*c* can be any suitable material, preferably thermoplastic material or other thermoformable, such as draw formable, material. Several examples of suitable materials follow. More than one type of material can be used for a given parenteral container, for example if a double walled or other more complex container is formed. An olefin polymer (for example polypropylene (PP) or polyethylene (PE)); a cyclic olefin copolymer (COC); a cyclic olefin polymer (COP); polymethylpentene; a polyester (for example polyethylene terephthalate, polyethylene naphthalate, or polybutylene terephthalate (PBT)); PVdC (polyvinylidene chloride); polyvinyl chloride (PVC); polycarbonate; polylactic acid; polystyrene, hydrogenated polystyrene; poly(cyclohexylethylene) (PCHE); epoxy resin; nylon; polyurethane polyacrylonitrile (PAN); polyacrylonitrile (PAN); an ionomeric resin (for example Surlyn®); glass (for example borosilicate glass); or a combination of any two or more of these. Presently preferred materials include a cyclic olefin polymer, a polyethylene terephthalate or a polypropylene; and more preferably COP.

COP and COC are high purity, moisture barrier, clear, and sterilization compatible resins, which make them excellent alternatives to glass in a wide range of medical products. However, it should be noted that COP is a very different polymer compared to COC in terms of coating adhesion, clarity, ductility and melt processing. For example ZEONEX®690R (COP) may be contrasted to TOPAS® 6013M-07 (COC) in regards to physical properties and performance properties. The ZEONEX® is a more ductile material, has better clarity, and it does not shatter as easily when dropped. This COP also has lower extractables, which is a decided advantage with pharmaceutical packaging. The following table summarizes some of these differences:

TABLE 1

Comparative properties of COP and COC

| Resin | COP | COC |
|---|---|---|
| Elongation at yield | 20% | 2.6% |
| Tensile modulus | 341.4 ksi or 1519 kN | 421 ksi or 1873 kN |
| Tg (° C.) | 136 | 142 |
| Drop impact | Won't shatter easily when dropped | Shatters easily when dropped |

TABLE 1-continued

Comparative properties of COP and COC

| Resin | COP | COC |
|---|---|---|
| Extractables | Lower | Higher |
| Purity | Contains less low MW additives or process aids | Contains more low Mw additives or process aids |

For the containers herein, according to the invention, cyclic olefin polymers (COPs) are preferred as the materials for the containers. COP is derived from a bulky cyclic olefin, such as norbornene. This may be achieved by ring-opening metathesis polymerization (ROMP) and subsequent hydrogenation of C=C. In contrast, cyclic olefin copolymers (COC) are produced by chain copolymerization of cyclic monomers such as 8,9,10-trinorborn-2-ene (norbornene) or 1,2,3,4,4a,5,8,8a-octahydro-1,4:5,8-dimethanonaphthalene (tetracyclododecene) with ethylene (such as TOPAS® Advanced Polymer's TOPAS® and Mitsui Chemical's APEL®). The chemical structures in regards to the synthetic steps towards COC and COP are shown below.

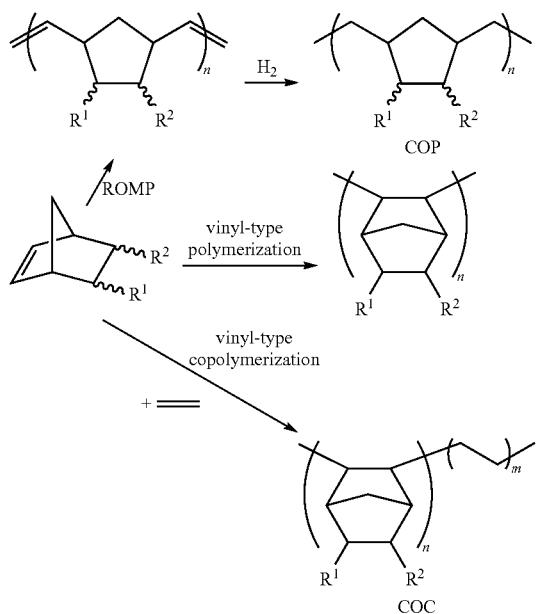

It is preferable to use high-purity cycloolefin polymers. The COP polymers are available from Zeon under the trade name ZEONEX®. They are distinguished by high break resistance, high transparency and high heat, radiation and chemical resistance. They are free of ions and heavy metals. They can be sterilized by means of autoclaving, ethylene oxide and gamma or electron radiation. In addition, they have pronounced barrier properties with respect to water vapor and oxygen. For example, ZEONEX® 690R, exhibits lower permeability to water vapor and oxygen than polypropylene.

A solid or liquid anti-static additive may be blended into the ORMOCER® coating solution formulation before curing, without adversely affecting the anti-scratch behavior of the ORMOCER® after curing. Anti-static additives which may be used in optional embodiment of the present invention include, for example ethoxylated alkyl amides, glycerol stearates, fatty acid esters, cationic polyacylates, esters or ethers of polyols and sodium alkyl sulfonates, quaternary ammonium compounds, and alkylphosphates. Commercial anti-stat materials can include Ciba IRGASTAT®, BASF LAROSTAT® 377, Cytec CYASTAT® LS, SN, or SP, Eastern Color and Chemical ECCOSTAT™ ASP, and Evonik ADDID®. Some particular materials finding use in the present disclosure include ADDID 240 or ADDID 230, which are liquid antistatic additives formulated from solid salts and quaternary nitrogen compounds, sold by Evonik Resource Efficiency GmbH, TEGO Products; Induquat ECR 956, a cationic polyacrylate dissolved in ethanol, sold by Indulor Chemie GmbH, Ankum, Germany; and Indunal ECR 774, an aqueous solution of polysodium styrene sulfonate, also sold by Indulor Chemie GmbH.

One embodiment may be an article (including a container) comprised of one or more interior coatings (for example, a tie coating or layer, a barrier coating or layer, and a pH protective coating or layer) on an interior wall of the article, wherein the article further has an anti-scratch-anti static coating on an exterior wall thereof.

The specification and drawings of patent application inventions for an interior layer or layers, and processes and equipment for applying such layer(s)—WO2014164928 and US20140251859—are incorporated here by reference in their entireties. The aforementioned patent applications describe a vessel comprising a thermoplastic wall in a container or article having an interior surface enclosing at least a portion of a lumen. The interior surface can be comprised of a tie coating or layer, a barrier coating or layer, and a pH protective coating or layer. The tie coating or layer is $SiO_xC_yH_z$ or $SiN_xC_yH_z$ in which x is from about 0.5 to about 2.4 as measured by X-ray photoelectron spectroscopy (XPS), y is from about 0.6 to about 3 as measured by XPS, and z is from about 2 to about 9 as preferably measured by Rutherford backscattering spectrometry (RBS), although it can alternatively be measured by hydrogen forward scattering (HFS). The tie coating or layer has an outer surface facing the internal surface (16) and the tie coating or layer has an interior surface.

The barrier coating or layer is $SiO_x$, in which x is between 1.5 and 2.9 as measured by XPS. The barrier coating or layer is applied by plasma enhanced chemical vapor deposition (PECVD). The barrier coating or layer is positioned between the interior surface of the tie coating or layer and the lumen, and is supported by the thermoplastic wall.

The pH protective coating or layer is $SiO_xC_yH_z$, in which x is between 0.5 and 2.4 as measured by XPS, y is between 0.6 and 3 as measured by XPS, and z is from about 2 to about 9 as measured by RBS, preferably, or hydrogen forward scattering (HFS), less preferably. The pH protective coating or layer is applied by PECVD, and is positioned between the barrier coating or layer and the lumen. The pH protective coating or layer and tie coating or layer together are effective to keep the barrier coating or layer at least substantially undissolved as a result of attack by a fluid contained in the lumen having a pH greater than 5, optionally a pH of 8, for a period of at least six months.

In any embodiment, the pharmaceutical or diagnostic fluid or other material 40 optionally can be any pharmaceutical material suitable for parenteral administration to a human. The pharmaceutical or diagnostic fluid or other material 40 optionally can be any diagnostic material. The pharmaceutical or diagnostic fluid or other material 40 optionally can be any anesthetic material suitable for administration to a human. Some non-limiting examples of suitable pharmaceutical or diagnostic materials follow. Any one or any combination of two or more of them can be used.

Injectable Drugs

Ablavar (Gadofosveset Trisodium Injection); Abarelix Depot; Abobotulinumtoxin A Injection (Dysport); ABT-263; ABT-869; ABX-EFG; Accretropin (Somatropin Injection); Acetadote (Acetylcysteine Injection); Acetazolamide Injection (Acetazolamide Injection); Acetylcysteine Injection (Acetadote); Actemra (Tocilizumab Injection); Acthrel (Corticorelin Ovine Triflutate for Injection); Actummune; Activase; Acyclovir for Injection (Zovirax Injection); Adacel; Adalimumab; Adenoscan (Adenosine Injection); Adenosine Injection (Adenoscan); Adrenaclick; AdreView (Iobenguane I 123 Injection for Intravenous Use); Afluria; Ak-Fluor (Fluorescein Injection); Aldurazyme (Laronidase); Alglucerase Injection (Ceredase); Alkeran Injection (Melphalan Hcl Injection); Allopurinol Sodium for Injection (Aloprim); Aloprim (Allopurinol Sodium for Injection); Alprostadil; Alsuma (Sumatriptan Injection); ALTU-238; Amino Acid Injections; Aminosyn; Apidra; Apremilast; Alprostadil Dual Chamber System for Injection (Caverject Impulse); AMG 009; AMG 076; AMG 102; AMG 108; AMG 114; AMG 162; AMG 220; AMG 221; AMG 222; AMG 223; AMG 317; AMG 379; AMG 386; AMG 403; AMG 477; AMG 479; AMG 517; AMG 531; AMG 557; AMG 623; AMG 655; AMG 706; AMG 714; AMG 745; AMG 785; AMG 811; AMG 827; AMG 837; AMG 853; AMG 951; Amiodarone HCl Injection (Amiodarone HCl Injection); Amobarbital Sodium Injection (Amytal Sodium); Amytal Sodium (Amobarbital Sodium Injection); Anakinra; Anti-Abeta; Anti-Beta7; Anti-Beta20; Anti-CD4; Anti-CD20; Anti-CD40; Anti-IFNalpha; Anti-IL13; Anti-OX40L; Anti-oxLDS; Anti-NGF; Anti-NRP1; Arixtra; Amphadase (Hyaluronidase Inj); Ammonul (Sodium Phenylacetate and Sodium Benzoate Injection); Anaprox; Anzemet Injection (Dolasetron Mesylate Injection); Apidra (Insulin Glulisine [rDNA origin] Inj); Apomab; Aranesp (darbepoetin alfa); Argatroban (Argatroban Injection); Arginine Hydrochloride Injection (R-Gene 10); Aristocort; Aristospan; Arsenic Trioxide Injection (Trisenox); Articane HCl and Epinephrine Injection (Septocaine); Arzerra (Ofatumumab Injection); Asclera (Polidocanol Injection); Ataluren; Ataluren-DMD; Atenolol Inj (Tenormin I.V. Injection); Atracurium Besylate Injection (Atracurium Besylate Injection); Avastin; Azactam Injection (Aztreonam Injection); Azithromycin (Zithromax Injection); Aztreonam Injection (Azactam Injection); Baclofen Injection (Lioresal Intrathecal); Bacteriostatic Water (Bacteriostatic Water for Injection); Baclofen Injection (Lioresal Intrathecal); Bal in Oil Ampules (Dimercarprol Injection); BayHepB; BayTet; Benadryl; Bendamustine Hydrochloride Injection (Treanda); Benztropine Mesylate Injection (Cogentin); Betamethasone Injectable Suspension (Celestone Soluspan); Bexxar; Bicillin C-R 900/300 (Penicillin G Benzathine and Penicillin G Procaine Injection); Blenoxane (Bleomycin Sulfate Injection); Bleomycin Sulfate Injection (Blenoxane); Boniva Injection (Ibandronate Sodium Injection); Botox Cosmetic (OnabotulinumtoxinA for Injection); BR3-FC; Bravelle (Urofollitropin Injection); Bretylium (Bretylium Tosylate Injection); Brevital Sodium (Methohexital Sodium for Injection); Brethine; Briobacept; BTT-1023; Bupivacaine HCl; Byetta; Ca-DTPA (Pentetate Calcium Trisodium Inj); Cabazitaxel Injection (Jevtana); Caffeine Alkaloid (Caffeine and Sodium Benzoate Injection); Calcijex Injection (Calcitrol); Calcitrol (Calcijex Injection); Calcium Chloride (Calcium Chloride Injection 10%); Calcium Disodium Versenate (Edetate Calcium Disodium Injection); Campath (Altemtuzumab); Camptosar Injection (Irinotecan Hydrochloride); Canakinumab Injection (Ilaris); Capastat Sulfate (Capreomycin for Injection); Capreomycin for Injection (Capastat Sulfate); Cardiolite (Prep kit for Technetium Tc99 Sestamibi for Injection); Carticel; Cathflo; Cefazolin and Dextrose for Injection (Cefazolin Injection); Cefepime Hydrochloride; Cefotaxime; Ceftriaxone; Cerezyme; Carnitor Injection; Caverject; Celestone Soluspan; Celsior; Cerebyx (Fosphenytoin Sodium Injection); Ceredase (Alglucerase Injection); Ceretec (Technetium Tc99m Exametazime Injection); Certolizumab; CF-101; Chloramphenicol Sodium Succinate (Chloramphenicol Sodium Succinate Injection); Chloramphenicol Sodium Succinate Injection (Chloramphenicol Sodium Succinate); Cholestagel (Colesevelam HCL); Choriogonadotropin Alfa Injection (Ovidrel); Cimzia; Cisplatin (Cisplatin Injection); Clolar (Clofarabine Injection); Clomiphine Citrate; Clonidine Injection (Duraclon); Cogentin (Benztropine Mesylate Injection); Colistimethate Injection (Coly-Mycin M); Coly-Mycin M (Colistimethate Injection); Compath; Conivaptan Hcl Injection (Vaprisol); Conjugated Estrogens for Injection (Premarin Injection); Copaxone; Corticorelin Ovine Triflutate for Injection (Acthrel); Corvert (Ibutilide Fumarate Injection); Cubicin (Daptomycin Injection); CF-101; Cyanokit (Hydroxocobalamin for Injection); Cytarabine Liposome Injection (DepoCyt); Cyanocobalamin; Cytovene (ganciclovir); D.H.E. 45; Dacetuzumab; Dacogen (Decitabine Injection); Dalteparin; Dantrium IV (Dantrolene Sodium for Injection); Dantrolene Sodium for Injection (Dantrium IV); Daptomycin Injection (Cubicin); Darbepoietin Alfa; DDAVP Injection (Desmopressin Acetate Injection); Decavax; Decitabine Injection (Dacogen); Dehydrated Alcohol (Dehydrated Alcohol Injection); Denosumab Injection (Prolia); Delatestryl; Delestrogen; Delteparin Sodium; Depacon (Valproate Sodium Injection); Depo Medrol (Methylprednisolone Acetate Injectable Suspension); Depo-Cyt (Cytarabine Liposome Injection); DepoDur (Morphine Sulfate XR Liposome Injection); Desmopressin Acetate Injection (DDAVP Injection); Depo-Estradiol; Depo-Provera 104 mg/ml; Depo-Provera 150 mg/ml; Depo-Testosterone; Dexrazoxane for Injection, Intravenous Infusion Only (Totect); Dextrose/Electrolytes; Dextrose and Sodium Chloride Inj (Dextrose 5% in 0.9% Sodium Chloride); Dextrose; Diazepam Injection (Diazepam Injection); Digoxin Injection (Lanoxin Injection); Dilaudid-HP (Hydromorphone Hydrochloride Injection); Dimercarprol Injection (Bal in Oil Ampules); Diphenhydramine Injection (Benadryl Injection); Dipyridamole Injection (Dipyridamole Injection); DMOAD; Docetaxel for Injection (Taxotere); Dolasetron Mesylate Injection (Anzemet Injection); Doribax (Doripenem for Injection); Doripenem for Injection (Doribax); Doxercalciferol Injection (Hectorol Injection); Doxil (Doxorubicin Hcl Liposome Injection); Doxorubicin Hcl Liposome Injection (Doxil); Duraclon (Clonidine Injection); Duramorph (Morphine Injection); Dysport (Abobotulinumtoxin A Injection); Ecallantide Injection (Kalbitor); EC-Naprosyn (naproxen); Edetate Calcium Disodium Injection (Calcium Disodium Versenate); Edex (Alprostadil for Injection); Engerix; Edrophonium Injection (Enlon); Eliglustat Tartate; Eloxatin (Oxaliplatin Injection); Emend Injection (Fosaprepitant Dimeglumine Injection); Enalaprilat Injection (Enalaprilat Injection); Enlon (Edrophonium Injection); Enoxaparin Sodium Injection (Lovenox); Eovist (Gadoxetate Disodium Injection); Enbrel (etanercept); Enoxaparin; Epicel; Epinepherine; Epipen; Epipen Jr.; Epratuzumab; Erbitux; Ertapenem Injection (Invanz); Erythropoieten; Essential Amino Acid Injection (Nephramine); Estradiol Cypionate; Estradiol Valerate; Etanercept; Exenatide Injection (Byetta); Evlotra; Fabrazyme (Adalsidase beta); Famotidine Injection; FDG (Fludeoxyglucose F 18 Injection);

Feraheme (Ferumoxytol Injection); Feridex I.V. (Ferumoxides Injectable Solution); Fertinex; Ferumoxides Injectable Solution (Feridex I.V.); Ferumoxytol Injection (Feraheme); Flagyl Injection (Metronidazole Injection); Fluarix; Fludara (Fludarabine Phosphate); Fludeoxyglucose F 18 Injection (FDG); Fluorescein Injection (Ak-Fluor); Follistim AQ Cartridge (Follitropin Beta Injection); Follitropin Alfa Injection (Gonal-f RFF); Follitropin Beta Injection (Follistim AQ Cartridge); Folotyn (Pralatrexate Solution for Intravenous Injection); Fondaparinux; Forteo (Teriparatide (rDNA origin) Injection); Fostamatinib; Fosaprepitant Dimeglumine Injection (Emend Injection); Foscarnet Sodium Injection (Foscavir); Foscavir (Foscarnet Sodium Injection); Fosphenytoin Sodium Injection (Cerebyx); Fospropofol Disodium Injection (Lusedra); Fragmin; Fuzeon (enfuvirtide); GA101; Gadobenate Dimeglumine Injection (Multihance); Gadofosveset Trisodium Injection (Ablavar); Gadoteridol Injection Solution (ProHance); Gadoversetamide Injection (OptiMARK); Gadoxetate Disodium Injection (Eovist); Ganirelix (Ganirelix Acetate Injection); Gardasil; GC1008; GDFD; Gemtuzumab Ozogamicin for Injection (Mylotarg); Genotropin; Gentamicin Injection; GENZ-112638; Golimumab Injection (Simponi Injection); Gonal-f RFF (Follitropin Alfa Injection); Granisetron Hydrochloride (Kytril Injection); Gentamicin Sulfate; Glatiramer Acetate; Glucagen; Glucagon; HAE1; Haldol (Haloperidol Injection); Havrix; Hectorol Injection (Doxercalciferol Injection); Hedgehog Pathway Inhibitor; Heparin; Herceptin; hG-CSF; Humalog; Human Growth Hormone; Humatrope; HuMax; Humegon; Humira; Humulin; Ibandronate Sodium Injection (Boniva Injection); Ibuprofen Lysine Injection (NeoProfen); Ibutilide Fumarate Injection (Corvert); Idamycin PFS (Idarubicin Hydrochloride Injection); Idarubicin Hydrochloride Injection (Idamycin PFS); Ilaris (Canakinumab Injection); Imipenem and Cilastatin for Injection (Primaxin I.V.); Imitrex; Incobotulinumtoxin A for Injection (Xeomin); Increlex (Mecasermin [rDNA origin] Injection); Indocin IV (Indomethacin Inj); Indomethacin Inj (Indocin IV); Infanrix; Innohep; Insulin; Insulin Aspart [rDNA origin] Inj (NovoLog); Insulin Glargine [rDNA origin] Injection (Lantus); Insulin Glulisine [rDNA origin] Inj (Apidra); Interferon alfa-2b, Recombinant for Injection (Intron A); Intron A (Interferon alfa-2b, Recombinant for Injection); Invanz (Ertapenem Injection); Invega Sustenna (Paliperidone Palmitate Extended-Release Injectable Suspension); Invirase (saquinavir mesylate); Iobenguane I 123 Injection for Intravenous Use (AdreView); Iopromide Injection (Ultravist); Ioversol Injection (Optiray Injection); Iplex (Mecasermin Rinfabate [rDNA origin] Injection); Iprivask; Irinotecan Hydrochloride (Camptosar Injection); Iron Sucrose Injection (Venofer); Istodax (Romidepsin for Injection); Itraconazole Injection (Sporanox Injection); Jevtana (Cabazitaxel Injection); Jonexa; Kalbitor (Ecallantide Injection); KCL in D5NS (Potassium Chloride in 5% Dextrose and Sodium Chloride Injection); KCL in D5W; KCL in NS; Kenalog 10 Injection (Triamcinolone Acetonide Injectable Suspension); Kepivance (Palifermin); Keppra Injection (Levetiracetam); Keratinocyte; KFG; Kinase Inhibitor; Kineret (Anakinra); Kinlytic (Urokinase Injection); Kinrix; Klonopin (clonazepam); Kytril Injection (Granisetron Hydrochloride); lacosamide Tablet and Injection (Vimpat); Lactated Ringer's; Lanoxin Injection (Digoxin Injection); Lansoprazole for Injection (Prevacid I.V.); Lantus; Leucovorin Calcium (Leucovorin Calcium Injection); Lente (L); Leptin; Levemir; Leukine Sargramostim; Leuprolide Acetate; Levothyroxine; Levetiracetam (Keppra Injection); Lovenox; Levocarnitine Injection (Carnitor Injection); Lexiscan (Regadenoson Injection); Lioresal Intrathecal (Baclofen Injection); Liraglutide [rDNA] Injection (Victoza); Lovenox (Enoxaparin Sodium Injection); Lucentis (Ranibizumab Injection); Lumizyme; Lupron (Leuprolide Acetate Injection); Lusedra (Fospropofol Disodium Injection); Maci; Magnesium Sulfate (Magnesium Sulfate Injection); Mannitol Injection (Mannitol IV); Marcaine (Bupivacaine Hydrochloride and Epinephrine Injection); Maxipime (Cefepime Hydrochloride for Injection); MDP Multidose Kit of Technetium Injection (Technetium Tc99m Medronate Injection); Mecasermin [rDNA origin] Injection (Increlex); Mecasermin Rinfabate [rDNA origin] Injection (Iplex); Melphalan Hcl Injection (Alkeran Injection); Methotrexate; Menactra; Menopur (Menotropins Injection); Menotropins for Injection (Repronex); Methohexital Sodium for Injection (Brevital Sodium); Methyldopate Hydrochloride Injection, Solution (Methyldopate Hcl); Methylene Blue (Methylene Blue Injection); Methylprednisolone Acetate Injectable Suspension (Depo Medrol); MetMab; Metoclopramide Injection (Reglan Injection); Metrodin (Urofollitropin for Injection); Metronidazole Injection (Flagyl Injection); Miacalcin; Midazolam (Midazolam Injection); Mimpara (Cinacalet); Minocin Injection (Minocycline Inj); Minocycline Inj (Minocin Injection); Mipomersen; Mitoxantrone for Injection Concentrate (Novantrone); Morphine Injection (Duramorph); Morphine Sulfate XR Liposome Injection (DepoDur); Morrhuate Sodium (Morrhuate Sodium Injection); Motesanib; Mozobil (Plerixafor Injection); Multihance (Gadobenate Dimeglumine Injection); Multiple Electrolytes and Dextrose Injection; Multiple Electrolytes Injection; Mylotarg (Gemtuzumab Ozogamicin for Injection); Myozyme (Alglucosidase alfa); Nafcillin Injection (Nafcillin Sodium); Nafcillin Sodium (Nafcillin Injection); Naltrexone XR Inj (Vivitrol); Naprosyn (naproxen); NeoProfen (Ibuprofen Lysine Injection); Nandrol Decanoate; Neostigmine Methylsulfate (Neostigmine Methylsulfate Injection); NEO-GAA; NeoTect (Technetium Tc 99m Depreotide Injection); Nephramine (Essential Amino Acid Injection); Neulasta (pegfilgrastim); Neupogen (Filgrastim); Novolin; Novolog; NeoRecormon; Neutrexin (Trimetrexate Glucuronate Inj); NPH (N); Nexterone (Amiodarone HCl Injection); Norditropin (Somatropin Injection); Normal Saline (Sodium Chloride Injection); Novantrone (Mitoxantrone for Injection Concentrate); Novolin 70/30 Innolet (70% NPH, Human Insulin Isophane Suspension and 30% Regular, Human Insulin Injection); NovoLog (Insulin Aspart [rDNA origin] Inj); Nplate (romiplostim); Nutropin (Somatropin (rDNA origin) for Inj); Nutropin AQ; Nutropin Depot (Somatropin (rDNA origin) for Inj); Octreotide Acetate Injection (Sandostatin LAR); Ocrelizumab; Ofatumumab Injection (Arzerra); Olanzapine Extended Release Injectable Suspension (Zyprexa Relprevv); Omnitarg; Omnitrope (Somatropin [rDNA origin] Injection); Ondansetron Hydrochloride Injection (Zofran Injection); OptiMARK (Gadoversetamide Injection); Optiray Injection (Ioversol Injection); Orencia; Osmitrol Injection in Aviva (Mannitol Injection in Aviva Plastic Vessel); Osmitrol Injection in Viaflex (Mannitol Injection in Viaflex Plastic Vessel); Osteoprotegrin; Ovidrel (Choriogonadotropin Alfa Injection); Oxacillin (Oxacillin for Injection); Oxaliplatin Injection (Eloxatin); Oxytocin Injection (Pitocin); Paliperidone Palmitate Extended-Release Injectable Suspension (Invega Sustenna); Pamidronate Disodium Injection (Pamidronate Disodium Injection); Panitumumab Injection for Intravenous Use (Vectibix); Papaverine Hydrochloride Injection (Papaverine Injection); Papaverine Injection (Papaverine Hydrochloride Injection); Parathyroid Hormone; Paricalcitol Injection Fliptop Vial (Zemplar Injection);

PARP Inhibitor; Pediarix; PEGIntron; Peginterferon; Pegfilgrastim; Penicillin G Benzathine and Penicillin G Procaine; Pentetate Calcium Trisodium Inj (Ca-DTPA); Pentetate Zinc Trisodium Injection (Zn-DTPA); Pepcid Injection (Famotidine Injection); Pergonal; Pertuzumab; Phentolamine Mesylate (Phentolamine Mesylate for Injection); Physostigmine Salicylate (Physostigmine Salicylate (injection)); Physostigmine Salicylate (injection) (Physostigmine Salicylate); Piperacillin and Tazobactam Injection (Zosyn); Pitocin (Oxytocin Injection); Plasma-Lyte 148 (Multiple Electrolytes Inj); Plasma-Lyte 56 and Dextrose (Multiple Electrolytes and Dextrose Injection in Viaflex Plastic Vessel); Plasma-Lyte; Plerixafor Injection (Mozobil); Polidocanol Injection (Asclera); Potassium Chloride; Pralatrexate Solution for Intravenous Injection (Folotyn); Pramlintide Acetate Injection (Symlin); Premarin Injection (Conjugated Estrogens for Injection); Prep kit for Technetium Tc99 Sestamibi for Injection (Cardiolite); Prevacid I.V. (Lansoprazole for Injection); Primaxin I.V. (Imipenem and Cilastatin for Injection); Prochymal; Procrit; Progesterone; ProHance (Gadoteridol Injection Solution); Prolia (Denosumab Injection); Promethazine HCl Injection (Promethazine Hydrochloride Injection); Propranolol Hydrochloride Injection (Propranolol Hydrochloride Injection); Quinidine Gluconate Injection (Quinidine Injection); Quinidine Injection (Quinidine Gluconate Injection); R-Gene 10 (Arginine Hydrochloride Injection); Ranibizumab Injection (Lucentis); Ranitidine Hydrochloride Injection (Zantac Injection); Raptiva; Reclast (Zoledronic Acid Injection); Recombivarix HB; Regadenoson Injection (Lexiscan); Reglan Injection (Metoclopramide Injection); Remicade; Renagel; Renvela (Sevelamer Carbonate); Repronex (Menotropins for Injection); Retrovir IV (Zidovudine Injection); rhApo2L/TRAIL; Ringer's and 5% Dextrose Injection (Ringers in Dextrose); Ringer's Injection (Ringers Injection); Rituxan; Rituximab; Rocephin (ceftriaxone); Rocuronium Bromide Injection (Zemuron); Roferon-A (interferon alfa-2a); Romazicon (flumazenil); Romidepsin for Injection (Istodax); Saizen (Somatropin Injection); Sandostatin LAR (Octreotide Acetate Injection); Sclerostin Ab; Sensipar (cinacalcet); Sensorcaine (Bupivacaine HCl Injections); Septocaine (Articane HCl and Epinephrine Injection); Serostim LQ (Somatropin (rDNA origin) Injection); Simponi Injection (Golimumab Injection); Sodium Acetate (Sodium Acetate Injection); Sodium Bicarbonate (Sodium Bicarbonate 5% Injection); Sodium Lactate (Sodium Lactate Injection in AVIVA); Sodium Phenylacetate and Sodium Benzoate Injection (Ammonul); Somatropin (rDNA origin) for Inj (Nutropin); Sporanox Injection (Itraconazole Injection); Stelara Injection (Ustekinumab); Stemgen; Sufenta (Sufentanil Citrate Injection); Sufentanil Citrate Injection (Sufenta); Sumavel; Sumatriptan Injection (Alsuma); Symlin; Symlin Pen; Systemic Hedgehog Antagonist; Synvisc-One (Hylan G-F 20 Single Intra-articular Injection); Tarceva; Taxotere (Docetaxel for Injection); Technetium Tc 99m; Telavancin for Injection (Vibativ); Temsirolimus Injection (Torisel); Tenormin I.V. Injection (Atenolol Inj); Teriparatide (rDNA origin) Injection (Forteo); Testosterone Cypionate; Testosterone Enanthate; Testosterone Propionate; Tev-Tropin (Somatropin, rDNA Origin, for Injection); tgAAC94; Thallous Chloride; Theophylline; Thiotepa (Thiotepa Injection); Thymoglobulin (Anti-Thymocyte Globulin (Rabbit); Thyrogen (Thyrotropin Alfa for Injection); Ticarcillin Disodium and Clavulanate Potassium Galaxy (Timentin Injection); Tigan Injection (Trimethobenzamide Hydrochloride Injectable); Timentin Injection (Ticarcillin Disodium and Clavulanate Potassium Galaxy); TNKase; Tobramycin Injection (Tobramycin Injection); Tocilizumab Injection (Actemra); Torisel (Temsirolimus Injection); Totect (Dexrazoxane for Injection, Intravenous Infusion Only); Trastuzumab-DM1; Travasol (Amino Acids (Injection)); Treanda (Bendamustine Hydrochloride Injection); Trelstar (Triptorelin Pamoate for Injectable Suspension); Triamcinolone Acetonide; Triamcinolone Diacetate; Triamcinolone Hexacetonide Injectable Suspension (Aristospan Injection 20 mg); Triesence (Triamcinolone Acetonide Injectable Suspension); Trimethobenzamide Hydrochloride Injectable (Tigan Injection); Trimetrexate Glucuronate Inj (Neutrexin); Triptorelin Pamoate for Injectable Suspension (Trelstar); Twinject; Trivaris (Triamcinolone Acetonide Injectable Suspension); Trisenox (Arsenic Trioxide Injection); Twinrix; Typhoid Vi; Ultravist (Iopromide Injection); Urofollitropin for Injection (Metrodin); Urokinase Injection (Kinlytic); Ustekinumab (Stelara Injection); Ultralente (U); Valium (diazepam); Valproate Sodium Injection (Depacon); Valtropin (Somatropin Injection); Vancomycin Hydrochloride (Vancomycin Hydrochloride Injection); Vancomycin Hydrochloride Injection (Vancomycin Hydrochloride); Vaprisol (Conivaptan Hcl Injection); VAQTA; Vasovist (Gadofosveset Trisodium Injection for Intravenous Use); Vectibix (Panitumumab Injection for Intravenous Use); Venofer (Iron Sucrose Injection); Verteporfin Inj (Visudyne); Vibativ (Telavancin for Injection); Victoza (Liraglutide [rDNA] Injection); Vimpat (lacosamide Tablet and Injection); Vinblastine Sulfate (Vinblastine Sulfate Injection); Vincasar PFS (Vincristine Sulfate Injection); Victoza; Vincristine Sulfate (Vincristine Sulfate Injection); Visudyne (Verteporfin Inj); Vitamin B-12; Vivitrol (Naltrexone XR Inj); Voluven (Hydroxyethyl Starch in Sodium Chloride Injection); Xeloda; Xenical (orlistat); Xeomin (Incobotulinumtoxin A for Injection); Xolair; Zantac Injection (Ranitidine Hydrochloride Injection); Zemplar Injection (Paricalcitol Injection Fliptop Vial); Zemuron (Rocuronium Bromide Injection); Zenapax (daclizumab); Zevalin; Zidovudine Injection (Retrovir IV); Zithromax Injection (Azithromycin); Zn-DTPA (Pentetate Zinc Trisodium Injection); Zofran Injection (Ondansetron Hydrochloride Injection); Zingo; Zoledronic Acid for Inj (Zometa); Zoledronic Acid Injection (Reclast); Zometa (Zoledronic Acid for Inj); Zosyn (Piperacillin and Tazobactam Injection); Zyprexa Relprevv (Olanzapine Extended Release Injectable Suspension)

Liquid Drugs (Non-Injectable)

Abilify; AccuNeb (Albuterol Sulfate Inhalation Solution); Actidose Aqua (Activated Charcoal Suspension); Activated Charcoal Suspension (Actidose Aqua); Advair; Agenerase Oral Solution (Amprenavir Oral Solution); Akten (Lidocaine Hydrochloride Ophthalmic Gel); Alamast (Pemirolast Potassium Ophthalmic Solution); Albumin (Human) 5% Solution (Buminate 5%); Albuterol Sulfate Inhalation Solution; Alinia; Alocril; Alphagan; Alrex; Alvesco; Amprenavir Oral Solution; Analpram-HC; Arformoterol Tartrate Inhalation Solution (Brovana); Aristospan Injection 20 mg (Triamcinolone Hexacetonide Injectable Suspension); Asacol; Asmanex; Astepro; Astepro (Azelastine Hydrochloride Nasal Spray); Atrovent Nasal Spray (Ipratropium Bromide Nasal Spray); Atrovent Nasal Spray 0.06; Augmentin ES-600; Azasite (Azithromycin Ophthalmic Solution); Azelaic Acid (Finacea Gel); Azelastine Hydrochloride Nasal Spray (Astepro); Azelex (Azelaic Acid Cream); Azopt (Brinzolamide Ophthalmic Suspension); Bacteriostatic Saline; Balanced Salt; Bepotastine; Bactroban Nasal; Bactroban; Beclovent; Benzac W; Betimol; Betoptic S; Bepreve; Bimatoprost Ophthalmic Solution; Bleph 10 (Sulfacetamide Sodium Ophthalmic Solution 10%); Brinzolamide Ophthalmic Suspension (Azopt); Bromfenac Ophthalmic Solution (Xibrom); Bromhist; Brovana (Arformoterol Tartrate Inhalation Solution); Budesonide Inhalation Suspension (Pulmicort Respules); Cambia (Diclofenac Potassium for Oral Solution); Capex; Carac; Carboxine-PSE; Carnitor; Cayston (Aztreonam for Inhalation Solution); Cellcept; Centany; Cerumenex; Ciloxan Ophthalmic Solution (Ciprofloxacin HCL Ophthalmic Solution); Ciprodex; Ciprofloxacin HCL Ophthalmic Solution (Ciloxan Ophthalmic Solution); Clemastine Fumarate Syrup (Clemastine Fumarate Syrup); CoLyte (PEG Electrolytes Solution); Combiven; Comtan; Condylox; Cordran; Cortisporin Ophthalmic Suspension; Cortisporin Otic Suspension; Cromolyn Sodium Inhalation Solution (Intal Nebulizer Solution); Cromolyn Sodium Ophthalmic Solution (Opticrom); Crystalline Amino Acid Solution with Electrolytes (Aminosyn Electrolytes); Cutivate; Cuvposa (Glycopyrrolate Oral Solution); Cyanocobalamin (CaloMist Nasal Spray); Cyclosporine Oral Solution (Gengraf Oral Solution); Cyclogyl; Cysview (Hexaminolevulinate Hydrochloride Intravesical Solution); DermOtic Oil (Fluocinolone Acetonide Oil Ear Drops); Desmopressin Acetate Nasal Spray; DDAVP; Derma-Smoothe/FS; Dexamethasone Intensol; Dianeal Low Calcium; Dianeal PD; Diclofenac Potassium for Oral Solution (Cambia); Didanosine Pediatric Powder for Oral Solution (Videx); Differin; Dilantin 125 (Phenytoin Oral Suspension); Ditropan; Dorzolamide Hydrochloride Ophthalmic Solution (Trusopt); Dorzolamide Hydrochloride-Timolol Maleate Ophthalmic Solution (Cosopt); Dovonex Scalp (Calcipotriene Solution); Doxycycline Calcium Oral Suspension (Vibramycin Oral); Efudex; Elaprase (Idursulfase Solution); Elestat (Epinastine HCl Ophthalmic Solution); Elocon; Epinastine HCl Ophthalmic Solution (Elestat); Epivir HBV; Epogen (Epoetin alfa); Erythromycin Topical Solution 1.5% (Staticin); Ethiodol (Ethiodized Oil); Ethosuximide Oral Solution (Zarontin Oral Solution); Eurax; Extraneal (Icodextrin Peritoneal Dialysis Solution); Felbatol; Feridex I.V. (Ferumoxides Injectable Solution); Flovent; Floxin Otic (Ofloxacin Otic Solution); Flo-Pred (Prednisolone Acetate Oral Suspension); Fluoroplex; Flunisolide Nasal Solution (Flunisolide Nasal Spray 0.025%); Fluorometholone Ophthalmic Suspension (FML); Flurbiprofen Sodium Ophthalmic Solution (Ocufen); FML; Foradil; Formoterol Fumarate Inhalation Solution (Perforomist); Fosamax; Furadantin (Nitrofurantoin Oral Suspension); Furoxone; Gammagard Liquid (Immune Globulin Intravenous (Human) 10%); Gantrisin (Acetyl Sulfisoxazole Pediatric Suspension); Gatifloxacin Ophthalmic Solution (Zymar); Gengraf Oral Solution (Cyclosporine Oral Solution); Glycopyrrolate Oral Solution (Cuvposa); Halcinonide Topical Solution (Halog Solution); Halog Solution (Halcinonide Topical Solution); HEP-LOCK U/P (Preservative-Free Heparin Lock Flush Solution); Heparin Lock Flush Solution (Hepflush 10); Hexaminolevulinate Hydrochloride Intravesical Solution (Cysview); Hydrocodone Bitartrate and Acetaminophen Oral Solution (Lortab Elixir); Hydroquinone 3% Topical Solution (Melquin-3 Topical Solution); IAP Antagonist; Isopto; Ipratropium Bromide Nasal Spray (Atrovent Nasal Spray); Itraconazole Oral Solution (Sporanox Oral Solution); Ketorolac Tromethamine Ophthalmic Solution (Acular LS); Kaletra; Lanoxin; Lexiva; Leuprolide Acetate for Depot Suspension (Lupron Depot 11.25 mg); Levobetaxolol Hydrochloride Ophthalmic Suspension (Betaxon); Levocarnitine Tablets, Oral Solution, Sugar-Free (Carnitor); Levofloxacin Ophthalmic Solution 0.5% (Quixin); Lidocaine HCl Sterile Solution (Xylocaine MPF Sterile Solution); Lok Pak (Heparin Lock Flush Solution); Lorazepam Intensol; Lortab Elixir (Hydrocodone Bitartrate and Acetaminophen Oral Solution); Lotemax (Loteprednol Etabonate Ophthalmic Suspension); Loteprednol Etabonate Ophthalmic Suspension (Alrex); Low Calcium Peritoneal Dialysis Solutions (Dianeal Low Calcium); Lumigan (Bimatoprost Ophthalmic Solution 0.03% for Glaucoma); Lupron Depot 11.25 mg (Leuprolide Acetate for Depot Suspension); Megestrol Acetate Oral Suspension (Megestrol Acetate Oral Suspension); MEK Inhibitor; Mepron; Mesnex; Mestinon; Mesalamine Rectal Suspension Enema (Rowasa); Melquin-3 Topical Solution (Hydroquinone 3% Topical Solution); MetMab; Methyldopate Hcl (Methyldopate Hydrochloride Injection, Solution); Methylin Oral Solution (Methylphenidate HCl Oral Solution 5 mg/5 mL and 10 mg/5 mL); Methylprednisolone Acetate Injectable Suspension (Depo Medrol); Methylphenidate HCl Oral Solution 5 mg/5 mL and 10 mg/5 mL (Methylin Oral Solution); Methylprednisolone sodium succinate (Solu Medrol); Metipranolol Ophthalmic Solution (Optipranolol); Migranal; Miochol-E (Acetylcholine Chloride Intraocular Solution); Micro-K for Liquid Suspension (Potassium Chloride Extended Release Formulation for Liquid Suspension); Minocin (Minocycline Hydrochloride Oral Suspension); Nasacort; Neomycin and Polymyxin B Sulfates and Hydrocortisone; Nepafenac Ophthalmic Suspension (Nevanac); Nevanac (Nepafenac Ophthalmic Suspension); Nitrofurantoin Oral Suspension (Furadantin); Noxafil (Posaconazole Oral Suspension); Nystatin (oral) (Nystatin Oral Suspension); Nystatin Oral Suspension (Nystatin (oral)); Ocufen (Flurbiprofen Sodium Ophthalmic Solution); Ofloxacin Ophthalmic Solution (Ofloxacin Ophthalmic Solution); Ofloxacin Otic Solution (Floxin Otic); Olopatadine Hydrochloride Ophthalmic Solution (Pataday); Opticrom (Cromolyn Sodium Ophthalmic Solution); Optipranolol (Metipranolol Ophthalmic Solution); Patanol; Pediapred; PerioGard; Phenytoin Oral Suspension (Dilantin 125); Phisohex; Posaconazole Oral Suspension (Noxafil); Potassium Chloride Extended Release Formulation for Liquid Suspension (Micro-K for Liquid Suspension); Pataday (Olopatadine Hydrochloride Ophthalmic Solution); Patanase Nasal Spray (Olopatadine Hydrochloride Nasal Spray); PEG Electrolytes Solution (CoLyte); Pemirolast Potassium Ophthalmic Solution (Alamast); Penlac (Ciclopirox Topical Solution); PENNSAID (Diclofenac Sodium Topical Solution); Perforomist (Formoterol Fumarate Inhalation Solution); Peritoneal Dialysis Solution; Phenylephrine Hydrochloride Ophthalmic Solution (Neo-Synephrine); Phospholine Iodide (Echothiophate Iodide for Ophthalmic Solution); Podofilox (Podofilox Topical Solution); Pred Forte (Prednisolone Acetate Ophthalmic Suspension); Pralatrexate Solution for Intravenous Injection (Folotyn); Pred Mild; Prednisone Intensol; Prednisolone Acetate Ophthalmic Suspension (Pred Forte); Prevacid; PrismaSol Solution (Sterile Hemofiltration Hemodiafiltration Solution); ProAir; Proglycem; ProHance (Gadoteridol Injection Solution); Proparacaine Hydrochloride Ophthalmic Solution (Alcaine); Propine; Pulmicort; Pulmozyme; Quixin (Levofloxacin Ophthalmic Solution 0.5%); QVAR; Rapamune; Rebetol; Relacon-HC; Rotarix (Rotavirus Vaccine, Live, Oral Suspension); Rotavirus Vaccine, Live, Oral Suspension (Rotarix); Rowasa (Mesalamine Rectal Suspension Enema); Sabril (Vigabatrin Oral Solution); Sacrosidase Oral Solution (Sucraid); Sandimmune; Sepra; Serevent Diskus; Solu Cortef (Hydrocortisone Sodium Succinate); Solu Medrol (Methylprednisolone sodium succinate); Spiriva; Sporanox Oral Solution (Itraconazole Oral Solution); Staticin (Erythromycin Topical Solution 1.5%); Stalevo; Starlix; Sterile Hemofiltration Hemodiafiltration Solution (PrismaSol Solution); Stimate;

Sucralfate (Carafate Suspension); Sulfacetamide Sodium Ophthalmic Solution 10% (Bleph 10); Synarel Nasal Solution (Nafarelin Acetate Nasal Solution for Endometriosis); Taclonex Scalp (Calcipotriene and Betamethasone Dipropionate Topical Suspension); Tamiflu; Tobi; TobraDex; Tobradex ST (Tobramycin/Dexamethasone Ophthalmic Suspension 0.3%/0.05%); Tobramycin/Dexamethasone Ophthalmic Suspension 0.3%/0.05% (Tobradex ST); Timolol; Timoptic; Travatan Z; Treprostinil Inhalation Solution (Tyvaso); Trusopt (Dorzolamide Hydrochloride Ophthalmic Solution); Tyvaso (Treprostinil Inhalation Solution); Ventolin; Vfend; Vibramycin Oral (Doxycycline Calcium Oral Suspension); Videx (Didanosine Pediatric Powder for Oral Solution); Vigabatrin Oral Solution (Sabril); Viokase; Viracept; Viramune; Vitamin K1 (Fluid Colloidal Solution of Vitamin K1); Voltaren Ophthalmic (Diclofenac Sodium Ophthalmic Solution); Zarontin Oral Solution (Ethosuximide Oral Solution); Ziagen; Zyvox; Zymar (Gatifloxacin Ophthalmic Solution); Zymaxid (Gatifloxacin Ophthalmic Solution).

Drug Classes 5-alpha-reductase inhibitors; 5-aminosalicylates; 5HT3 receptor antagonists; adamantane antivirals; adrenal cortical steroids; adrenal corticosteroid inhibitors; adrenergic bronchodilators; agents for hypertensive emergencies; agents for pulmonary hypertension; aldosterone receptor antagonists; alkylating agents; alpha-adrenoreceptor antagonists; alpha-glucosidase inhibitors; alternative medicines; amebicides; aminoglycosides; aminopenicillins; aminosalicylates; amylin analogs; Analgesic Combinations; Analgesics; androgens and anabolic steroids; angiotensin converting enzyme inhibitors; angiotensin II inhibitors; anorectal preparations; anorexiants; antacids; anthelmintics; anti-angiogenic ophthalmic agents; anti-CTLA-4 monoclonal antibodies; anti-infectives; antiadrenergic agents, centrally acting; antiadrenergic agents, peripherally acting; antiandrogens; antianginal agents; antiarrhythmic agents; antiasthmatic combinations; antibiotics/antineoplastics; anticholinergic antiemetics; anticholinergic antiparkinson agents; anticholinergic bronchodilators; anticholinergic chronotropic agents; anticholinergics/antispasmodics; anticoagulants; anticonvulsants; antidepressants; antidiabetic agents; antidiabetic combinations; antidiarrheals; antidiuretic hormones; antidotes; antiemetic/antivertigo agents; antifungals; antigonadotropic agents; antigout agents; antihistamines; antihyperlipidemic agents; antihyperlipidemic combinations; antihypertensive combinations; antihyperuricemic agents; antimalarial agents; antimalarial combinations; antimalarial quinolines; antimetabolites; antimigraine agents; antineoplastic detoxifying agents; antineoplastic interferons; antineoplastic monoclonal antibodies; antineoplastics; antiparkinson agents; antiplatelet agents; antpseudomonal penicillins; antipsoriatics; antipsychotics; antirheumatics; antiseptic and germicides; antithyroid agents; antitoxins and antivenins; antituberculosis agents; antituberculosis combinations; antitussives; antiviral agents; antiviral combinations; antiviral interferons; anxiolytics, sedatives, and hypnotics; aromatase inhibitors; atypical antipsychotics; azole antifungals; bacterial vaccines; barbiturate anticonvulsants; barbiturates; BCR-ABL tyrosine kinase inhibitors; benzodiazepine anticonvulsants; benzodiazepines; beta-adrenergic blocking agents; beta-lactamase inhibitors; bile acid sequestrants; biologicals; bisphosphonates; bone resorption inhibitors; bronchodilator combinations; bronchodilators; calcitonin; calcium channel blocking agents; carbamate anticonvulsants; carbapenems; carbonic anhydrase inhibitor anticonvulsants; carbonic anhydrase inhibitors; cardiac stressing agents; cardioselective beta blockers; cardiovascular agents; catecholamines; CD20 monoclonal antibodies; CD33 monoclonal antibodies; CD52 monoclonal antibodies; central nervous system agents; cephalosporins; cerumenolytics; chelating agents; chemokine receptor antagonist; chloride channel activators; cholesterol absorption inhibitors; cholinergic agonists; cholinergic muscle stimulants; cholinesterase inhibitors; CNS stimulants; coagulation modifiers; colony stimulating factors; contraceptives; corticotropin; coumarins and indandiones; cox-2 inhibitors; decongestants; dermatological agents; diagnostic radiopharmaceuticals; dibenzazepine anticonvulsants; digestive enzymes; dipeptidyl peptidase 4 inhibitors; diuretics; dopaminergic antiparkinsonism agents; drugs used in alcohol dependence; echinocandins; EGFR inhibitors; estrogen receptor antagonists; estrogens; expectorants; factor Xa inhibitors; fatty acid derivative anticonvulsants; fibric acid derivatives; first generation cephalosporins; fourth generation cephalosporins; functional bowel disorder agents; gallstone solubilizing agents; gamma-aminobutyric acid analogs; gamma-aminobutyric acid reuptake inhibitors; gamma-aminobutyric acid transaminase inhibitors; gastrointestinal agents; general anesthetics; genitourinary tract agents; GI stimulants; glucocorticoids; glucose elevating agents; glycopeptide antibiotics; glycoprotein platelet inhibitors; glycylcyclines; gonadotropin releasing hormones; gonadotropin-releasing hormone antagonists; gonadotropins; group I antiarrhythmics; group II antiarrhythmics; group III antiarrhythmics; group IV antiarrhythmics; group V antiarrhythmics; growth hormone receptor blockers; growth hormones; *H. pylori* eradication agents; H2 antagonists; hematopoietic stem cell mobilizer; heparin antagonists; heparins; HER2 inhibitors; herbal products; histone deacetylase inhibitors; hormone replacement therapy; hormones; hormones/antineoplastics; hydantoin anticonvulsants; illicit (street) drugs; immune globulins; immunologic agents; immunosuppressive agents; impotence agents; in vivo diagnostic biologicals; incretin mimetics; inhaled anti-infectives; inhaled corticosteroids; inotropic agents; insulin; insulin-like growth factor; integrase strand transfer inhibitor; interferons; intravenous nutritional products; iodinated contrast media; ionic iodinated contrast media; iron products; ketolides; laxatives; leprostatics; leukotriene modifiers; lincomycin derivatives; lipoglycopeptides; local injectable anesthetics; loop diuretics; lung surfactants; lymphatic staining agents; lysosomal enzymes; macrolide derivatives; macrolides; magnetic resonance imaging contrast media; mast cell stabilizers; medical gas; meglitinides; metabolic agents; methylxanthines; mineralocorticoids; minerals and electrolytes; miscellaneous agents; miscellaneous analgesics; miscellaneous antibiotics; miscellaneous anticonvulsants; miscellaneous antidepressants; miscellaneous antidiabetic agents; miscellaneous antiemetics; miscellaneous antifungals; miscellaneous antihyperlipidemic agents; miscellaneous antimalarials; miscellaneous antineoplastics; miscellaneous antiparkinson agents; miscellaneous antipsychotic agents; miscellaneous antituberculosis agents; miscellaneous antivirals; miscellaneous anxiolytics, sedatives and hypnotics; miscellaneous biologicals; miscellaneous bone resorption inhibitors; miscellaneous cardiovascular agents; miscellaneous central nervous system agents; miscellaneous coagulation modifiers; miscellaneous diuretics; miscellaneous genitourinary tract agents; miscellaneous GI agents; miscellaneous hormones; miscellaneous metabolic agents; miscellaneous ophthalmic agents; miscellaneous otic agents; miscellaneous respiratory agents; miscellaneous sex hormones; miscellaneous topical agents; miscellaneous uncategorized agents; miscellaneous vaginal agents; mitotic inhibitors; monoamine oxidase inhibitors; monoclonal antibodies; mouth and throat products; mTOR inhibitors; mTOR kinase inhibitors; mucolytics; multikinase inhibitors; muscle relaxants; mydriatics; narcotic analgesic combinations; narcotic analgesics; nasal anti-infectives; nasal antihistamines and decongestants; nasal lubricants and irrigations; nasal preparations; nasal steroids; natural penicillins; neuraminidase inhibitors; neuromuscular blocking agents; next generation cephalosporins; nicotinic acid derivatives; nitrates; NNRTIs; non-cardioselective beta blockers; non-iodinated contrast media; non-ionic iodinated contrast media; non-sulfonylureas; non-steroidal anti-inflammatory agents; norepinephrine reuptake inhibitors; norepinephrine-dopamine reuptake inhibitors; nucleoside reverse transcriptase inhibitors (NRTIs); nutraceutical products; nutritional products; ophthalmic anesthetics; ophthalmic anti-infectives; ophthalmic anti-inflammatory agents; ophthalmic antihistamines and decongestants; ophthalmic diagnostic agents; ophthalmic glaucoma agents; ophthalmic lubricants and irrigations; ophthalmic preparations; ophthalmic steroids; ophthalmic steroids with anti-infectives; ophthalmic surgical agents; oral nutritional supplements; otic anesthetics; otic anti-infectives; otic preparations; otic steroids; otic steroids with anti-infectives; oxazolidinedione anticonvulsants; parathyroid hormone and analogs; penicillinase resistant penicillins; penicillins; peripheral opioid receptor antagonists; peripheral vasodilators; peripherally acting antiobesity agents; phenothiazine antiemetics; phenothiazine antipsychotics; phenylpiperazine antidepressants; plasma expanders; platelet aggregation inhibitors; platelet-stimulating agents; polyenes; potassium-sparing diuretics; probiotics; progesterone receptor modulators; progestins; prolactin inhibitors; prostaglandin D2 antagonists; protease inhibitors; proton pump inhibitors; psoralens; psychotherapeutic agents; psychotherapeutic combinations; purine nucleosides; pyrrolidine anticonvulsants; quinolones; radiocontrast agents; radiologic adjuncts; radiologic agents; radiologic conjugating agents; radiopharmaceuticals; RANK ligand inhibitors; recombinant human erythropoietins; renin inhibitors; respiratory agents; respiratory inhalant products; rifamycin derivatives; salicylates; sclerosing agents; second generation cephalosporins; selective estrogen receptor modulators; selective serotonin reuptake inhibitors; serotonin-norepinephrine reuptake inhibitors; serotoninergic neuroenteric modulators; sex hormone combinations; sex hormones; skeletal muscle relaxant combinations; skeletal muscle relaxants; smoking cessation agents; somatostatin and somatostatin analogs; spermicides; statins; sterile irrigating solutions; streptomyces derivatives; succinimide anticonvulsants; sulfonamides; sulfonylureas; synthetic ovulation stimulants; tetracyclic antidepressants; tetracyclines; therapeutic radiopharmaceuticals; thiazide diuretics; thiazolidinediones; thioxanthenes; third generation cephalosporins; thrombin inhibitors; thrombolytics; thyroid drugs; tocolytic agents; topical acne agents; topical agents; topical anesthetics; topical anti-infectives; topical antibiotics; topical antifungals; topical antihistamines; topical antipsoriatics; topical antivirals; topical astringents; topical debriding agents; topical depigmenting agents; topical emollients; topical keratolytics; topical steroids; topical steroids with anti-infectives; toxoids; triazine anticonvulsants; tricyclic antidepressants; trifunctional monoclonal antibodies; tumor necrosis factor (TNF) inhibitors; tyrosine kinase inhibitors; ultrasound contrast media; upper respiratory combinations; urea anticonvulsants; urinary anti-infectives; urinary antispasmodics; urinary pH modifiers; uterotonic agents; vaccine; vaccine combinations; vaginal anti-infectives; vaginal preparations; vasodilators; vasopressin antagonists; vasopressors; VEGF/VEGFR inhibitors; viral vaccines; viscosupplementation agents; vitamin and mineral combinations; vitamins Diagnostic Tests 17-Hydroxyprogesterone; ACE (Angiotensin I converting enzyme); Acetaminophen; Acid phosphatase; ACTH; Activated clotting time; Activated protein C resistance; Adrenocorticotropic hormone (ACTH); Alanine aminotransferase (ALT); Albumin; Aldolase; Aldosterone; Alkaline phosphatase; Alkaline phosphatase (ALP); Alpha1-antitrypsin; Alpha-fetoprotein; Alpha-fetoprotien; Ammonia levels; Amylase; ANA (antinuclear antbodies); ANA (antinuclear antibodies); Angiotensin-converting enzyme (ACE); Anion gap; Anticardiolipin antibody; Anticardiolipin antivbodies (ACA); Anti-centromere antibody; Antidiuretic hormone; Anti-DNA; Anti-Dnase-B; Anti-Gliadin antibody; Antiglomerular basement membrane antibody; Anti-HBc (Hepatitis B core antibodies; Anti-HBs (Hepatitis B surface antibody; Antiphospholipid antibody; Anti-RNA polymerase; Anti-Smith (Sm) antibodies; Anti-Smooth Muscle antibody; Antistreptolysin O (ASO); Antithrombin III; Anti-Xa activity; Anti-Xa assay; Apolipoproteins; Arsenic; Aspartate aminotransferase (AST); B12; Basophil; Beta-2-Microglobulin; Beta-hydroxybutyrate; B-HCG; Bilirubin; Bilirubin, direct; Bilirubin, indirect; Bilirubin, total; Bleeding time; Blood gases (arterial); Blood urea nitrogen (BUN); BUN; BUN (blood urea nitrogen); CA 125; CA 15-3; CA 19-9; Calcitonin; Calcium; Calcium (ionized); Carbon monoxide (CO); Carcinoembryonic antigen (CEA); CBC; CEA; CEA (carcinoembryonic antigen); Ceruloplasmin; CH50Chloride; Cholesterol; Cholesterol, HDL; Clot lysis time; Clot retraction time; CMP; CO2; Cold agglutinins; Complement C3; Copper; Corticotrophin releasing hormone (CRH) stimulation test; Cortisol; Cortrosyn stimulation test; C-peptide; CPK (Total); CPK-MB; C-reactive protein; Creatinine; Creatinine kinase (CK); Cryoglobulins; DAT (Direct antiglobulin test); D-Dimer; Dexamethasone suppression test; DHEA-S; Dilute Russell viper venom; Elliptocytes; Eosinophil; Erythrocyte sedimentation rate (ESR); Estradiol; Estriol; Ethanol; Ethylene glycol; Euglobulin lysis; Factor V Leiden; Factor VIII inhibitor; Factor VIII level; Ferritin; Fibrin split products; Fibrinogen; Folate; Folate (serum; Fractional excretion of sodium (FENA); FSH (follicle stimulating factor); FTA-ABS; Gamma glutamyl transferase (GGT); Gastrin; GGTP (Gamma glutamyl transferase); Glucose; Growth hormone; Haptoglobin; HBeAg (Hepatitis Be antigen); HBs-Ag (Hepatitis B surface antigen); *Helicobacter pylori*; Hematocrit; Hematocrit (HCT); Hemoglobin; Hemoglobin A1C; Hemoglobin electrophoresis; Hepatitis A antibodies; Hepatitis C antibodies; IAT (Indirect antiglobulin test); Immunofixation (IFE); Iron; Lactate dehydrogenase (LDH); Lactic acid (lactate); LDH; LH (Leutinizing hormone; Lipase; Lupus anticoagulant; Lymphocyte; Magnesium; MCH (mean corpuscular hemoglobin; MCHC (mean corpuscular hemoglobin concentration); MCV (mean corpuscular volume); Methylmalonate; Monocyte; MPV (mean platelet volume); Myoglobin; Neutrophil; Parathyroid hormone (PTH); Phosphorus; Platelets (plt); Potassium; Prealbumin; Prolactin; Prostate specific antigen (PSA); Protein C; Protein S; PSA (prostate specific antigen); PT (Prothrombin time); PTT (Partial thromboplastin time); RDW (red cell distribution width); Renin; Rennin; Reticulocyte count; reticulocytes; Rheumatoid factor (RF); Sed Rate; Serum glutamic-pyruvic transaminase (SGPT); Serum protein electrophoresis (SPEP); Sodium; T3-resin uptake (T3RU); T4, Free; Thrombin time; Thyroid stimulating hormone (TSH); Thyroxine (T4); Total iron binding capacity (TIBC); Total protein; Transferrin; Transferrin saturation; Triglyceride (TG); Troponin; Uric acid; Vitamin B12; White blood cells (WBC); Widal test.

A pharmaceutical vessel as previously described containing a fluid is contemplated in any embodiment, in which the fluid comprises a drug based on messenger RNA (mRNA), having the structure and characteristics disclosed in the following patent documents, which are incorporated by reference in full in this specification, except that none of the claims are incorporated by reference: US20150086612; WO2013143683; WO2014072061; WO2012072096; US20140030808; US20140178438; US20120195917; US20110311584; WO2012159643; WO2014075788; WO2014075697; WO2014082729.

The invention, in regards to an exterior coating is explained in greater detail by the following Examples, but without the scope of the invention being limited thereby.

EXAMPLES

Example 1

The exterior coated plastics containers can be produced by the following process:
Injection blow mold COP containers
Atmospheric pressure corona-type air plasma pre-treatment
Coating of the COP containers with an ORMOCER lacquer by vacuum vapor deposition, immersion, flood-coating, pouring, injection, spraying or brush application, preferably by spraying
Full hardening of the lacquer by UV or IR radiation or heat treatment at from 60 to 150° C., especially at 130° C.

Example 2

The following is a representative formulation for an exterior coated plastic container containing a scratch resistant and anti-static coating.

| Process Sequence | Process Step/Additive |
| --- | --- |
| Substrate | Vials made of ZEONEX ® 690R |
| Pre-treatment | Atmospheric pressure corona-type air plasma pre-treatment, wipe with acetone and blow off with compressed air |
| Lacquer | ABRASIL ® GA2, VM, VA, or FAP plus antistatic additive: IRGASTAT ®, LAROSTAT ® 377, CYASTAT ® LS, SN, or SP, ECCOSTAT ™ ASP, and Evonik ADDID ® |
| Application Procedure | Dip-coating, drying process |
| Cure/Hardening | UV-curing: 3-5/cm$^2$ Thermal heating at 130° C. for 1 hour |

The COP vials are pretreated with an atmospheric pressure corona-type air plasma before lacquering. This creates Si—OH groups on the surface that can bind to the inorganic-organic coating. In one embodiment one of the following lacquer(s)—ABRASIL® VM, VA, VAD, FAP, or GA2 is applied in Example 2 by a spraying process. The full hardening of the lacquer layer is effected in an oven at around 130° C./1 hour. The film/coating adheres well to the surface of the container. This is shown by a layer adhesion test by means of the cross-cut test (DIN ISO 2409).

The coated vials are washed in a container-washing machine and dried in a sterilization tunnel. The containers are filled with an Oxaliplatin ([(1R,2R)-cyclohexane-1,2-diamine](ethanedioato-O,O')platinum(II)) solution in a filling/capping apparatus (for example VSR F01 from Bosch/Strunk) and then autoclaved at least 121° C./2 bar/15 min. After passing through the filling apparatus, the containers have no visible scratches.

TABLE 2

Comparative properties of COP with/without scratch/anti-stat coating

| Sample | Adhesion | Scratch Resistance | Static Sensor measurements KV/inch (KV/cm) |
| --- | --- | --- | --- |
| COP with No coating | NA | poor | 2.63 (1.04) |
| COP with ORMOCER ® Scratch coating | good | good | 1.3 (0.51) |
| COP with ORMOCER ® Scratch coating and anti-stat | good | good | <0.60 (0.24) |

Tests:
Adhesion—cross-cut tape test (DIN IS o) 2409)
Scratch: Scotch-Brite® Abrasion—The Scotch-Brite® Abrasion Test measures coating resistance to constant scrubbing with a standard abrasive scouring pad. The vertical load on the scouring pad is set at 10 pounds (4.54 kg), and the scouring pad is changed every 10,000 strokes. The number of cycles that are required to scrape the coating down to bare plastic is determined in order to gauge the abrasion resistance of the coating system.
Anti-Stat: Measurement using Static Sensor (KV/inch)-measures voltages associated with an electrostatic charge build-up on a surface-3M Static Sensor 718.

The amounts of the anti-static additives in polymers typically vary from 0.1% to 3% by weight. These additives are effective in different amounts at reducing the static charges of plastic articles that incorporate them. However, depending upon the anti-stat additive some are more efficacious than others in the polymer matrix and some tend to bloom more easily to the surface. Additives that bloom to the surface can contaminate the surface and the contents, especially liquid contents, of a container made from a polymer with such additives.

Furthermore, the container according to an aspect the invention may be provided with a hybrid organic-inorganic polymeric coating (for example, (ORMOCER®) comprising, consisting essentially of, or consisting of:
(i) a hydrolytic condensate, prepared from a silane of the formula $R_mSiX_{4-m}$ having the following meanings:
  R=crosslinkable organic radical
  X=hydrolyzable and condensable group
  m=1 or 2 or 3 (with 1 being preferred)
with a metal compound.
(ii) a prepolymer that is crosslinkable with the radicals R of the silane,
(iii) one or more (especially one or two) optional non-crosslinkable organofunctional silane(s) and
(iv) an optional low-volatility oxide.

For the container according to the invention, R in the silane formula can be a radical from the group formed by alkyl, alkenyl, alkynyl, aryl, arylalkyl, alkylaryl, arylalkenyl, alkenylaryl, arylalkynyl and alkynylaryl, it being possible for those radicals to be interrupted one or more times by an O atom and/or an S atom and/or an N atom and/or by an NH group, or to have a terminal OH, SH or $NH_2$ group. A radical such as R or R' "interrupted" as used in this specification has the structure $R_a$—Y—$R_b$—, in which $R_a$—$R_b$— meets the definition of R in the silane formula and Y is a linking group, here —O—, —S—, —N<, and/or —NH—.

For the container according to the invention, the radicals R in the silane formula can be, independently of one another, an unsubstituted radical or a radical substituted by one or more substituents from the group formed by halogen atoms, unsubstituted amino, amide, aldehyde, keto, alkylcarbonyl, carboxy, mercapto, cyano, isocyano, cyanato, isocyanato, hydroxy, alkoxy, alkoxycarbonyl, sulfonic acid, phosphoric acid, acrylic, acryloxy, methacrylic, methacryloxy, glycidyl, glycidyloxy, epoxy and vinyl groups and such groups in substituted form.

For the container according to the invention, the radicals X in the silane formula can be, independently of one another, alkoxy groups, aryloxy groups, acyloxy groups, alkyl-carbonyl groups, alkoxycarbonyl groups, hydroxy groups, halogen, hydrogen or substituted or unsubstituted amino groups.

For the container according to the invention, a prepolymer can be provided which carries a group R as reactive group, R having a meaning as detailed above.

Thus, for the container according to the invention a prepolymer can be provided which carries a group R as reactive group, R in the prepolymer and in the silane having the same meaning.

Furthermore, for the container according to the invention the silane and the prepolymer can be a combination as follows:
(i) silane having epoxy groups with epoxy resin as prepolymer and/or
(ii) silane having vinyl radicals with prepolymer having crosslinkable double bonds and/or
(iii) silane having polymerizable double bonds with prepolymer having crosslinkable double bonds and/or
(iv) mercapto-group-containing silane with prepolymer having crosslinkable double bonds and/or
(v) isocyanate-group-containing silane with polyol as prepolymer and/or
(vi) hydroxyl-group-containing silane with isocyanate as prepolymer and/or
(vii) amino-group-containing silane with epoxy resin as prepolymer.

Thus, the container according to the invention can be provided with a hydrolytic condensate of an acrylic-group-containing silane and with a prepolymer acrylate.

Furthermore, for the container according to the invention an optional non-crosslinkable organofunctional silane of the formula $R'_mSiX_{4-m}$ having the following meanings can be provided:
R'=non-crosslinkable organic radical
X=hydrolyzable and condensable group
m=1 or 2 or 3.

For the container according to the invention, R' in the silane formula can be a radical from the group formed by alkyl, cycloalkyl, aryl, arylalkyl and alkylaryl, it being possible for those radicals to be interrupted one or more times by an O atom and/or an S atom and/or an N atom and/or by an NH group or to have a terminal OH, SH or NH2 group.

Furthermore, for the container according to the invention, the radicals R' in the silane formula can be, independently of one another, an unsubstituted radical or a radical substituted by one or more substituents from the group formed by halogen atoms, unsubstituted amide, aldehyde, keto, alkylcarbonyl, carboxy, cyano, alkoxy and alkoxycarbonyl groups and such groups in substituted form.

Furthermore, for the container according to the invention the radicals X in the silane formula R'mSiX4-m can be, independently of one another, alkoxy groups, aryloxy groups, alkylcarbonyl groups, alkoxycarbonyl groups, hydroxy groups, halogen, hydrogen or substituted or unsubstituted amino groups.

Furthermore, for the container according to the invention a low-volatility oxide of compounds of elements of main group Ia, IIa, IIIa, IVa and/or Va or of sub-group IIb, IIIb, Vb, VIb, VIIb and/or VIIIb, with the exception of aluminum, can be provided.

Thus, for the container according to the invention B2O3, P2O5 and/or SnO2 can be provided.

Furthermore, the container according to the invention can be provided with an inorganic-organic hybrid polymer coating like ABRASIL® lacquer (commercial lacquers from Topcoating such as ABRASIL® VM, VA FAP or GA2) and anti-stats like ethoxylated alkylamines, ethoxylated alkyl amides, glycerol stearates, fatty acid esters, esters or ethers of polyols, sodium alkyl sulfonates, quaternary ammonium compounds, and alkylphosphates.

Furthermore, the container according to the invention can have a cylindrical or prismatic or square shape.

Furthermore, the container according to the invention can be an injection molded or blow injection molded container, a screw-closure container or an ampoule.

Furthermore, the container according to the invention can be an injection container or screw-closure container having a volume of from 1 to 1000 ml.

Furthermore, the container according to the invention can be an injection container having a volume of from 2 to 100 ml.

Furthermore, the container according to the invention can be an ampoule having a volume of from 1 to 20 ml.

Furthermore, the container according to the invention can be provided with an external anti-scratch (and optionally anti-stat) coating having a thickness of from 1 to 100 μm, especially from 2 to 30 μm and preferably from 8 to 20 μm.

The container according to the invention can be provided filled with a pharmaceutical preparation and closed with a closure.

The term alkyl refers to a saturated, straight-chain or branched hydrocarbon group having especially from 1 to 20 carbon atoms, preferably from 1 to 12 carbon atoms, more especially from 1 to 6 carbon atoms, for example the methyl, ethyl, propyl, isopropyl, n-butyl, isobutyl, tert-butyl, n-hexyl, 2,2-dimethylbutyl or n-octyl group.

The terms alkenyl and alkynyl refer to at least partially unsaturated, straight-chain or branched hydrocarbon groups having especially from 2 to 20 carbon atoms, preferably from 2 to 12 carbon atoms, more preferably from 2 to 6 carbon atoms, for example the ethenyl, allyl, acetylenyl, propargyl, isoprenyl or hex-2-enyl group. Preferably, alkenyl groups have one or two (preferably one) double bond(s) and alkynyl groups have one or two (preferably one) triple bond(s).

The term cycloalkyl refers to a cyclic group that has one or more rings (preferably 1 or 2) and contains especially from 3 to 14 ring carbon atoms, preferably from 3 to 10 ring carbon atoms. Examples are the cyclopropyl, cyclobutyl, cyclopentyl and cyclohexyl group.

The term aryl or Ar refers to an aromatic group that has one or more rings having especially from 6 to 14 ring carbon atoms, preferably from 6 to 10 (especially 6) ring carbon atoms. Examples are the phenyl, naphthyl or biphenyl group.

The terms arylalkyl, alkylaryl, arylalkenyl, alkenylaryl, arylalkynyl and alkynylaryl refer to groups which, in accordance with the above definitions, contain both aryl and alkyl, alkenyl or alkynyl groups. Specific examples are toluene, xylene, mesitylene, styrene, benzyl and cumene. Such a group preferably contains one or two aromatic rings having from 6 to 10 ring carbon atoms and one or two alkyl, alkenyl and/or alkynyl groups having from 1 or 2 to 6 carbon atoms.

Examples of non-crosslinkable organofunctional silanes are: bis-(dimethylamino)-methylphenylsilanes, bis-(mono-n-butylamino)dimethylsilanes, 2-chloroethyltrichloro-silanes, 2-chloroethylmethyldichlorosilanes, di-n-butyldichlorosilanes, diethyldiethoxysilanes, ethyltrimethoxysilanes, 8-bromooctyltrichlorosilanes, 3-bromoprop yltrichlorosilanes, tert-butyltrichlorosilanes, 1-chloroethyltrichlorosilanes, chloromethyltrichloro-silanes, chlorophenyltrichlorosilanes, cyclohexyltrichlorosilanes, dimethyldichlorosilanes, diphenyldichlorosilanes, ethyldichlorosilanes. Special preference is given to phenyltrimethoxysilane, aminopropyltriethoxysilane and propyltrimethoxysilane.

Examples of crosslinkable organofunctional silanes are vinyltrimethoxysilane, amino-propyltriethoxysilane, isocyanatopropyltriethoxysilane, mercaptopropyltrimethoxy-silane, vinyltriethoxysilanes, vinylethyldichlorosilanes, vinylmethyldiacetoxysilanes, vinylmethyldichlorosilanes, vinylmethyldiethoxysilanes, vinyltriacetoxysilanes, vinyltrichlorosilanes, phenylvinyldiethoxysilanes, phenylallyldichlorosilanes, 3-isocyanoto-poryltriethoxysilanes, 3-isocyanatopropyltriethoxysilanes, methacryloxypropenyltrimethoxylsilanes, 3-methacryloxypropyltrimethoxysilanes. Special preference is given to methacryloxypropyltrimethoxysilane and 3-glycidyloxypropyltrimethoxysilane.

Examples of metal compounds are: $TiCl_4$, $ZrCl_4$, $Ti(OC_2H_5)_4$, $Ti(OC_3H_7)_4$, $Ti(O\text{-}iso\text{-}C_3H_7)_4$, $Ti(OC_4H_9)_4$, $Zr(O\text{-}iso\text{-}C_3H_7)$, $Zr(OC_4H_9)_4$, $Ti(acetylacetonato)2(O\text{-}iso\text{-}C_3H_7)_2$, $Zr(acetylacetonato)_4$, $Ti(2\text{-}ethylhexyloxy)_4$ and other titanium or zirconium complexes with chelate ligands which are preferably coordinated by way of oxygen and/or nitrogen; $Al(OCH_3)_3$, $Al(OC_2H_5)_3$, $Al(O\text{-}n\text{-}C_3H_7)_3$, $Al(O\text{-}iso\text{-}C_3H_7)_3$, $Al(OC_4H_9)_3$, $Al(O\text{-}iso\text{-}C_4H_9)_3$, $Al(O\text{-}sec\text{-}C_4H_9)_3$, $AlCl_3$, $AlCl(OH)_2$, aluminum formate, aluminum acetate and aluminum oxalate as well as the corresponding (partially) chelated compounds, such as, for example, the acetylacetonates. Compounds that are liquid at room temperature, such as, for example, $Al(O\text{-}sec\text{-}C_4H_9)_3$ and $Al(O\text{-}iso\text{-}C_3H_7)_3$ are preferred.

ORMOCER® (organic modified ceramic) polymers are understood as being inorganic-organic hydride polymers. They are silicone polymers which are known as coating material for metals, glass, stone, etc. The preparation and composition of the inorganic-organic hybrid polymers are described, for example, in DE 43 03 570 C and EP0610831B1, both of which are incorporated by reference herein in their entireties.

For the synthesis of the hybrid polymers there are used functionalized silanes $R_mSiX_{4-m}$ wherein X is a hydrolyzable and condensable group and R is a cross-linkable organic radical. The groups X can be, independently of one another, alkoxy groups, aryloxy groups, acyloxy groups, alkylcarbonyl groups, alkoxycarbonyl groups, halogen, hydrogen or substituted or unsubstituted amino groups. The crosslinkable radical R can be alkyl, alkenyl, alkynyl, aryl, arylalkyl, alkylaryl, arylalkenyl, alkenylaryl, arylalkynyl, alkynylaryl, it being possible for those radicals to be interrupted by O, S or N atoms or by NH groups, or to have terminal OH, SH or NH2 groups, and to carry one or more substituents from the group of the halogens and substituted or unsubstituted amino, amide, aldehyde, keto, alkylcarbonyl, carboxy, mercapto, cyano, isocyano, cyanato, isocyanato, hydroxy, alkoxy, alkoxycarbonyl, sulfonic acid, phosphoric acid, acrylic, acryloxy, methacrylic, methacryloxy, epoxy, glycidyl, glycidyloxy or vinyl groups. The number m can have the value 1, 2 or 3. The compounds RmSiX4-m are combined with metal compounds such as halogen, alkyl, alkoxy, acyloxy or hydroxy compounds of aluminum, zirconium or titanium. The metal compounds can be oligomeric in chelate compound form. It may also be a complexed or non-complexed aluminum salt with an organic or inorganic acid. In addition to comprising a hydrolytic condensate of RmSiX4-m with a metal compound, the coating material comprises a prepolymer. The prepolymers can react with the crosslinkable groups R and thus serve the crosslinking. Preferably, the prepolymers can have reacting groups that are identical to the radical R of the compound RmSiX4-m. For example, in the case of acrylic-group-containing silanes, acrylates are used as prepolymer. The coating material can, in addition, contain non-crosslinkable organofunctional silanes, for example having alkyl or aryl groups, and/or low-volatility oxides.

The preparation and use of the inorganic-organic hybrid polymers is effected by the hydrolysis of the starting compounds to form a colloidal solution which contains the split-off hydrolysis products, for example the alcohols, and which is termed a lacquer. If applicable, it is also possible to add lacquer solvents. Such a lacquer can be applied to the material to be coated. Once the Si—O—Si network has been formed, the cross-linking of the organic molecule groups takes place. That can be effected by polymerization or polyaddition reactions.

As the inorganic-organic anti-scratch resistant coating material the following can be used: ORMOCER® lacquer, ABRASIL® GA2-30 or GA2-35, or ABRASIL® VM-26-IPA2. ABRASIL® GA2-30 is a thermally hardening hybrid lacquer having a high degree of scratch resistance, high moisture and chemical resistance, a high-gloss surface and high thermal resistance. ABRASIL® GA2-35, a variant of ABRASIL® GA2-30, is likewise a thermally hardening hydride lacquer. ABRASIL® GA2-35 is a preparation having hydrolyzed organically modified silicic acid esters, hydrolyzed aluminum alkoxide and a complex-former. Also optionally present are an epoxy resin and, as solvent, 2-butanol and methoxypropanol. ABRASIL® VM-26-IPA2 is a UV-hardening hybrid lacquer having a high degree of scratch resistance. Preferably, ORMOCER® lacquer, ABRASIL® GA2-30, and ABRASIL® GA2-35 are used.

The plastics containers according to the invention can be injection containers (=vial), screw-closure containers or ampoules.

The plastics containers can have a cylindrical shape or have a rectangular base. Injection containers or screw-closure containers can contain a volume of from 1 to 1000 ml. The volume of the injection containers is preferably from 2 to 100 ml. Ampoules can contain a volume of from 1 to 20 ml.

The plastics injection containers can be closed with rubber stoppers. Suitable materials for the rubber stoppers are chlorobutyl or bromobutyl rubber stoppers. The stopper can be provided with a crimped cap of a lightweight metal, for example of aluminum.

The screw-closure containers can be closed with a screw closure made, for example, of aluminum.

COP containers according to optional embodiments of the present invention may be produced by the following process: Injection blow molding of the COP containers; atmospheric pressure corona-type air plasma pre-treatment; coating of the COP containers with an ORMOCER® lacquer by means of vacuum vapor deposition, immersion, flood-coating, pouring, injection, spraying or brush application, preferably by spraying; and full hardening of the lacquer by UV or IR radiation or heat treatment at from 60 to 150° C., especially at 130° C.

The layer thickness of the ORMOCER® lacquer can be from 1 to 100 μm, especially from 2 to 30 μm. A layer thickness of from 8 to 20 μm is preferred.

Optionally a tie layer and/or a barrier layer can be applied to the COP substrate, and the ORMOCER®/anti-stat coating applied on top of it.

The ORMOCER® coated COP containers can be filled with a pharmaceutical preparation.

The ORMOCER® coated COP containers can be autoclaved, radiation-sterilized or sterilized with ethylene oxide.

The following is an optional method for filling containers according to an aspect of the present invention. The sterilized COP containers can be fed into the filling apparatus, the containers being pressed tightly against one another by a holding ring to prevent them from falling over. The containers are placed onto a conveyor belt with the aid of a turntable, the containers still being held tightly pressed together by means of a holding ring. The action of the turntable and the holding ring causes the containers to rub against one another, which in the case of uncoated plastics containers would result in their outer surfaces becoming scratched. The containers are transported by conveyor belt to the filling needles, where they are filled with the liquid in question. The containers are then closed with a rubber stopper and crimped cap.

The filled plastics containers according to the invention can be autoclaved. Autoclaving can be carried out at a temperature of at least 121° C., at a pressure of at least 2 bar for a period of at least 15 min. Alternatively, autoclaving at 110° C. and a longer period in the autoclave is possible.

The invention will be illustrated in more detail with reference to the following Examples, but it should be understood that the present invention is not deemed to be limited thereto.

Example 3

Coating with Anti-Scratch/Anti-Static Layer

Several vials were loaded onto vial spindles or holders on a chain conveyor using gloved hands. The vials were first exposed to ionized air to remove particles. Atmospheric pressure air plasma from two nozzles was then used to further clean and to activate the surface. Each vial was rotated in the plasma section with each nozzle 1 cm from the vial surface. One nozzle treated the top and the other treated the side as the vial passed. The process conditions were as follows: Plasma Power=20 kHz, Plasma cycle=100% (i.e. one continuous plasma impulse for the full length of treatment of one vessel), Plasma Voltage=260V and Plasma Amps=3.4 A.

The vials to be coated were rotated and sprayed with an ABRASIL inorganic-organic hybrid anti-scratch polymer blended with an ADDID liquid antistatic additive, a formulation of solid salts and quaternary nitrogen compounds sold by Evonik Industries AG, TEGO Products, using an ultrasonic sensor activated sprayer mounted on a slide. While spraying, the sprayer moved up and down on the slide as the vials were rotated past. The following setpoints were used: Horn Air=34 psi or pounds per square inch (230 kilopascals, KPa), Spray Air=34 psi (230 KPa), Needle Stroke=25 psi (170 KPa) and Pump Pressure=30 psi (200 KPa).

After the above spraying process was completed, the vials were heated, while facing up, using ceramic plate infrared heaters. The ceramic plate infrared heaters were heated up to about 320° C., resulting in local temperatures of 130° C. on the bottoms of the vials and 126° C. on the shoulders of the vials.

After the above infrared heating cycle was completed, the vials were pulled off from the vial spindles or holders by gloved hands, placed on a metal sheet, and then placed in an oven to cure the coating. The oven temperature used was 130° C. and the cure time used was 60 min.

Example 4

Anti-Scratch Effect Measurement

The purpose of this example was to show the effect of an anti-scratch and anti-static coating according to Example 3 for protection against scratching of the vials by a severe source of abrasion. Four coated test vials (A-D) and four uncoated control vials (E-H) were tested for transmittance before and after scratching. The unscratched vials were placed into a UV/VIS spectrophotometer (a spectrophotometer that has a spectrum including both ultraviolet and visible light) (Perkin Elmer model Lambda 45). The % Light Transmittance (% T) for each vial was measured between 400 nm and 500 nm visible light wavelengths at 1 nm intervals. The mean transmittance over the spectrum and the standard deviation for each unscratched vial A-H are shown in Table 3.

Each of the vials was then scratched by wrapping it in a Scotch-Brite® General Purpose Hand Pad 7447 (a substrate carrying a fine aluminum oxide abrasive, sold by 3M Company, St. Paul, Minn., USA) and rotating it three times by hand to scratch the vial. The vials were then placed back into the UV/VIS and the % Light Transmittance (% T) was measured again for the scratched vials A-H, again as reported in Table 3. The post scratching results were subtracted from the the pre-scratched results for the respective vials, to determine the difference in light transmittance (ΔT) between the scratched and unscratched vials. The comparing data are shown in Table 3. The average ΔT for coated vials A-D, before vs. after scratching, was 2.4%, indicating that scratching the coated vials caused little damage to their transmittance. The average ΔT for uncoated vials E-H, before vs. after scratching, was 25.4%, indicating that scratching the uncoated control vials E-H caused about 10 times as much change in transmittance. This data shows the value of the coating for reducing scratching.

TABLE 3

| Vial ID, Type | Mean % T, unscratched (Std. Dev.) | Mean % T, Scratched (Std. Dev.) | ΔT, % | AVG |
|---|---|---|---|---|
| A (coated) | 83.1 (0.5 | 82.1 (0.5) | 1.0 | A-D Avg. |
| B (coated) | 81.9 (0.5) | 77.5 (0.7) | 4.4 | 2.4 |

TABLE 3-continued

| Vial ID, Type | Mean % T, unscratched (Std. Dev.) | Mean % T, Scratched (Std. Dev.) | ΔT, % | AVG |
|---|---|---|---|---|
| C (coated) | 82.7 (0.6) | 79.9 (0.8) | 2.8 | |
| D (coated) | 82.8 (0.5 | 81.6 (0.5) | 1.2 | |
| E (uncoated) | 85.7 (0.7) | 61.1 (1.2) | 24.6 | E-H Avg. |
| F (uncoated) | 84.2 (0.2) | 62.0 (0.9) | 22.2 | 25.4 |
| G (uncoated) | 85.8 (0.5) | 50.4 (1.3) | 35.4 | |
| H (uncoated) | 85.6 (0.9) | 66.4 (1.4) | 19.2 | |

Example 5

Anti-Static Effect Measurement

The purpose of this example was to show the effect of the anti-scratch and anti-static coating according to Example 3 for reducing the absolute static electricity charge density on the coated containers and for increasing the rate of discharge of a static charge on the coated containers.

An uncharged coated vial, coated as described in Example 3, was placed in front of a Trek Model 511 Static Sensor, which was calibrated and grounded before taking any measurements. The static charge density, in kV/unit length, was recorded at 0 seconds and 10 seconds after the vial was placed in front of the sensor, using a calibrated stopwatch to track the time. The static charge on the uncharged, coated vial was 0.2325 kV/in. (0.0915 kV/cm) after 0 sec. (bar 62, FIG. 11 and Table 4), and 0.2225 kV/in. (0.0876 kV/cm) after 10 sec. (bar 64, FIG. 11 and Table 4). Comparing the results at 0 sec. vs. 10 sec., the rate of discharge was 4% in 10 sec.

Next, a static charge was placed on the vial by rubbing it with a silk cloth. The measurements were taken as before, and the results were recorded. The static charge on the charged, coated vial was 0.6400 kV/in. (0.252 kV/cm) after 0 sec. (bar 66, FIG. 11 and Table 4), and 0.5500 kV/in. (0.217 kV/cm) after 10 sec. (bar 64, FIG. 11 and Table 4). The rate of discharge in this instance was 14% in 10 sec.

Next, the same test was carried out again, except using a control vial having no coating. The static charge on the uncharged, uncoated vial was 0.513 kV/in. (0.202 kV/cm) after 0 sec. (bar 70, FIG. 11 and Table 4), and 0.503 kV/in. (0.198 kV/cm) after 10 sec. (bar 72, FIG. 11 and Table 4). Comparing the results at 0 sec. vs. 10 sec., the rate of discharge was 2% in 10 sec. The static charge on the charged, uncoated vial was 2.76 kV/in. (1.09 kV/cm) after 0 sec. (bar 74, FIG. 11 and Table 4), and 2.75 kV/in. (1.08 kV/cm) after 10 sec. (bar 76, FIG. 11 and Table 4). The rate of discharge in this instance was 0% in 10 sec.

This data showed that the present scratch and anti-static coating reduced the absolute static charge, with or without charging, and increased the rate at which the static charge was dissipated.

TABLE 4

Figure 11:
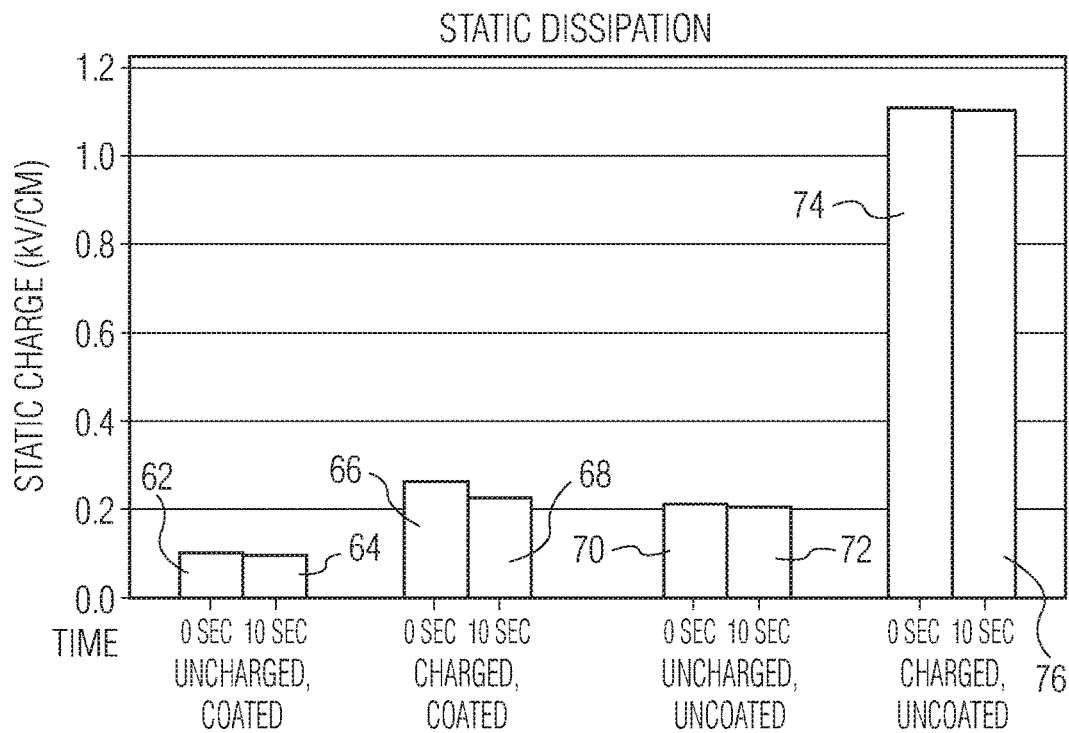
FIG. 11 is a plot of static dissipation at 0 and 10 seconds, displaying data from Example 5, Table 4.

| Condition | Time, sec. | kV/in | kV/cm | % Discharge per 10 sec. | Bar, FIG. 11 |
|---|---|---|---|---|---|
| COP, ORMOCER® Scratch and anti-static coating, uncharged | 0 | 0.2325 | 0.0915 | | 62 |
| COP, ORMOCER® Scratch and anti-static coating, uncharged | 10 | 0.2225 | 0.088 | 4% | 64 |
| COP, ORMOCER® Scratch and anti-static coating, charged | 0 | 0.6400 | 0.252 | | 66 |
| COP, ORMOCER® Scratch and anti-static coating/charged | 10 | 0.5500 | 0.217 | 14% | 68 |
| COP, No coating, uncharged | 0 | 0.5125 | 0.202 | | 70 |
| COP, No coating, uncharged | 10 | 0.5025 | 0.198 | 2% | 72 |
| COP, No coating, charged | 0 | 2.7575 | 1.086 | | 74 |
| COP, No coating, charged | 10 | 2.75 | 1.083 | 0% | 76 |

Example 6

Anti-Static Effect Measurement

Figure 12:
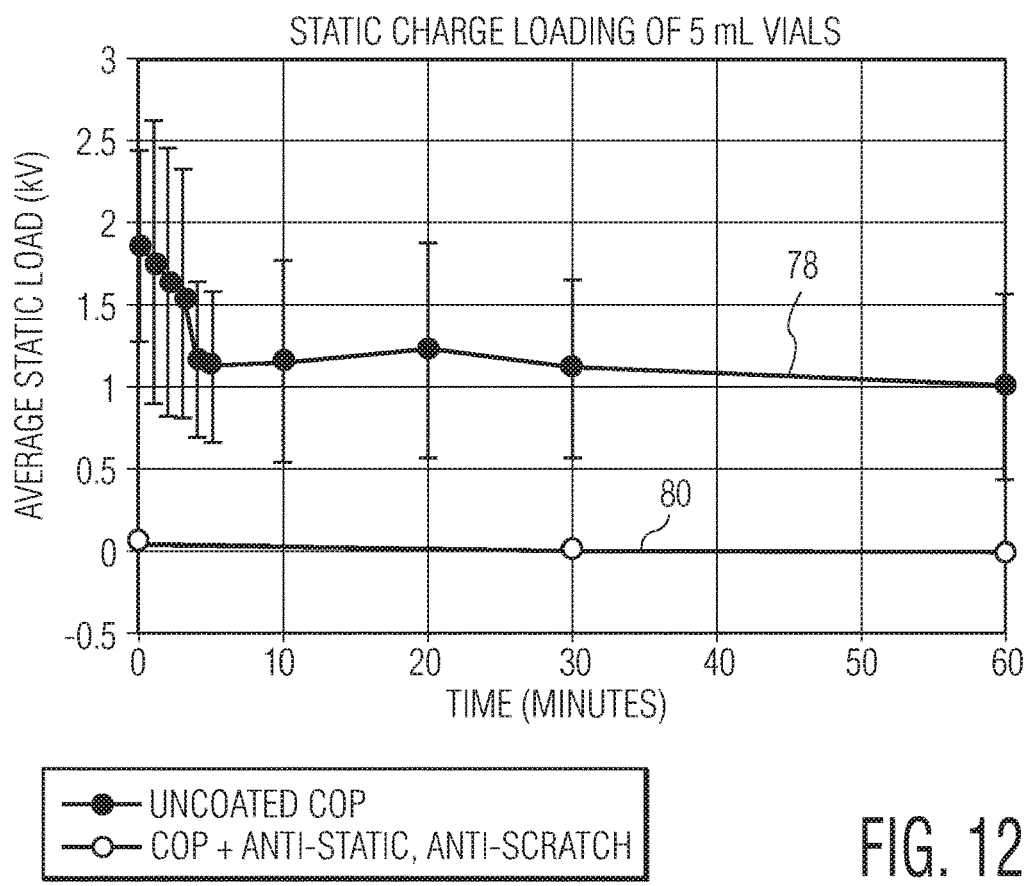
FIG. 12 is a plot of average static load versus time, displaying the data from Example 6.

This example showed the average static load (in kV) of 5 mL vials over a longer period, with and without the anti-static and anti-scratch coating described in Example 3. The coated and uncoated vials were charged as before, then the average static load was measured each minute from 0 to 5 minutes, and then at 10 minute intervals from 10 to 60 minutes. The results are shown in FIG. 12. The uncoated COP vials (plot 78) had a higher initial average static load, which decayed to about 1.3 kV over about 4 minutes, then remained relatively steady, remaining at 1 kV after 60 minutes. The coated COP vials (plot 80) had an average static load of about 0 kV throughout the 60-minute test, so the static load was substantially fully or fully discharged.

Example 7

The practical impact of applying the present coating of Example 3 is shown in FIGS. 13-14. A COP vial with the anti-static and anti-scratch coating of Example 3, shown in FIG. 13, was charged with static electricity as described in Example 2, then held by the top flange near an open petri dish containing cigarette ashes, representing ambient particulate contamination. The ashes were not attracted to the vial. When the test was repeated with the same type of vial except uncoated, as shown in FIG. 14, the cigarette ashes were attracted to the entire vial surface and distributed themselves over the vial surface.

Example 8

Vials coated with the anti-scratch and anti-static layer of Example 3 were boiled in MilliQ water at 100° C. for 24 hours. After the boiling process, the vials were visually inspected for any signs of delamination or other defects caused by the boiling. No coating delamination and other noticeable defects were observed on the coated surface of the vials. However, the uncoated inside of the vial had significant particulate contamination after boiling, indicating defects were caused by the boiling.

While the invention has been described in detail and with reference to specific examples thereof, it will be apparent to one skilled in the art that various changes and modifications can be made therein without departing from the spirit and scope thereof.

What is claimed:

1. A container comprising:
a wall made of a cycloolefin polymer having an internal surface enclosing a lumen and an contact surface, and an external anti-static and anti-scratch coating on the contact surface,
wherein the external anti-static and anti-scratch coating is optionally an inorganic-organic hybrid polymer coating comprising an anti-scratch agent and an anti-static agent.

2. A container as in claim 1 where the external anti-static and anti-scratch coating is sufficiently electrically conductive to substantially discharge a static charge.

3. A container as in claim 1, where the static load is less than 0.5 kV, preferably a static load of essentially 0 kV, most preferably a static load of 0 kV, after being subjected to an electrostatic charge and held for 60 minutes.

4. The container of claim 1, wherein the cycloolefin polymer consists essentially of COP resin.

5. The container of claim 1, wherein the container is an injection blow molded vial, syringe, blood tube, screw-closure container, or ampoule.

6. The container of claim 1 wherein the container is filled with a pharmaceutical preparation and closed with a closure.

7. The container of claim 1 where the anti-static additive is selected from the group of materials consisting of ethoxylated alkylamines, ethoxylated alkyl amides, glycerol stearates, fatty acid esters, esters or ethers of polyols, sodium alkyl sulfonates, cationic polyacrylates, quaternary ammonium compounds, alkylphosphates, and a combination of two or more of these.

8. The container of claim 1 where the anti-static additive is blended into the inorganic-organic hybrid polymer at about 0.1 to 3 weight percent.

9. The container of claim 1 which first undergoes an atmospheric pressure corona air-type plasma pre-treatment before the external anti-static and anti-scratch coating is applied.

10. The container of claim 1 where the external anti-static and anti-scratch coating is cured or hardened by UV or IR radiation or heat treatment at from 60 to 150° C.

11. The container of claim 1, wherein the external anti-static and anti-scratch coating is an inorganic-organic hybrid polymer comprising the reaction product of:
(i) a hydrolytic condensate, prepared from a metal compound and a silane of the formula $R_mSiX_{4-m}$, wherein R is a crosslinkable organic radical; X is a hydrolyzable and condensable group; m is 1, 2, or 3; and
(ii) a prepolymer that is crosslinked with the radical R of the silane of the hydrolytic condensate.

12. The container of claim 11, wherein R is selected from the group consisting of alkyl, alkenyl, alkynyl, aryl, arylalkyl, alkylaryl, arylalkenyl, alkenylaryl, arylalkynyl and alkynylaryl.

13. The container of claim 11, wherein each R is independently an unsubstituted radical or a radical substituted by one or more substituents selected from the group consisting of halogen, unsubstituted amino, amide, aldehyde, keto, alkylcarbonyl, carboxy, mercapto, cyano, isocyano, cyanato, isocyanato, hydroxy, alkoxy, alkoxycarbonyl, sulfonic acid, phosphoric acid, acrylic, acryloxy, methacrylic, methacryloxy, glycidyl, glycidyloxy, epoxy and vinyl groups.

14. The container of claim 11, wherein m is 2 or 3, and each R is independently an alkoxy, aryloxy, acyloxy, alkylcarbonyl, alkoxycarbonyl, hydroxy, halogen, hydrogen, or substituted or unsubstituted amino group.

15. The container of claim 11, wherein the prepolymer carries a reactive group, wherein the reactive group is an unsubstituted radical or a radical substituted by one or more substituents selected from the group consisting of halogen, unsubstituted amino, amide, aldehyde, keto, alkylcarbonyl, carboxy, mercapto, cyano, isocyano, cyanato, isocyanato, hydroxy, alkoxy, alkoxycarbonyl, sulfonic acid, phosphoric acid, acrylic, acryloxy, methacrylic, methacryloxy, glycidyl, glycidyloxy, epoxy and vinyl groups.

16. The container of claim 11, wherein the prepolymer carries a reactive group, and wherein the reactive group is the same as R of the silane of the hydrolytic condensate.

17. The container of claim 11, wherein the R is interrupted one or more times by one or more of an O, S, N or NH group, "interrupted" meaning that the radical R optionally has the structure $R_a$—Y—$R_b$— in which $R_a$—$R_b$— meets the definition of R in the silane formula and Y is a linking or interrupting group, here —O—, —S—, —N<, and/or —NH—.

18. The container of claim 11, wherein the R has a terminal OH, SH or $NH_2$ group.

19. The container of claim 11, wherein the inorganic-organic hybrid polymer comprises one or more non-crosslinkable organofunctional silanes.

20. The container of claim 19, wherein the non-crosslinkable organofunctional silane has the formula $R'_mSiX_{4-m}$, wherein R' is a non-crosslinkable organic radical; X is a hydrolyzable and condensable group; and m is 1, 2, or 3.

21. The container of claim 20, wherein R' is selected from the group consisting of alkyl, cycloalkyl, aryl, arylalkyl and alkylaryl.

22. The container of claim 20, wherein and each R' is independently an unsubstituted radical or a radical substituted by one or more substituents selected from the group consisting of halogen atoms, unsubstituted amide, aldehyde, keto, alkylcarbonyl, carboxy, cyano, alkoxy, alkoxycarbonyl groups.

23. The container of claim 20, wherein m is 1 or 2, and each X is independently an alkoxy, aryloxy, alkylcarbonyl, alkoxycarbonyl, hydroxy, halogen, hydrogen or substituted or unsubstituted amino group.

24. The container of claim 20, wherein R' is interrupted one or more times by one or more of an O, S, N, or NH group.

25. The container of claim 20, wherein R' has a terminal OH, SH or $NH_2$ group.

26. The container of claim 11, wherein the external anti-static and anti-scratch coating further comprises a low-volatility oxide.

27. The container of claim 26, wherein the low-volatility oxide comprises an element from
(i) main group Ia, IIa, IIIa, IVa or Va; or
(ii) sub-group IIb, IIIb, Vb, VIIb, VIIb or VIIIb, wherein the element is not aluminum.

28. The container of claim 26, wherein the low-volatility oxide comprises an element from
a. main group Ia, IIa, IIIa, IVa and Va; or
b. sub-group IIb, IIIb, Vb, VIb, VIIb and VIIIb, wherein the element is not aluminum.

29. The container of claim 11, wherein the prepolymer carries a reactive group, wherein the reactive group is alkyl, alkenyl, alkynyl, aryl, arylalkyl, alkylaryl, arylalkenyl, alkenylaryl, arylalkynyl and alkynylaryl.

30. The container of claim 29, wherein the reactive group is interrupted one or more times by one or more of an O, S, N or NH group.

31. The container of claim 29, wherein the reactive group has a terminal OH, SH or $NH_2$ group.

32. The container of claim 1, wherein the external antistatic and anti-scratch coating is an inorganic-organic hybrid polymer in which:
   (i) the silane has an epoxy group or epoxy groups, and the prepolymer is epoxy resin; or
   (ii) the silane has a vinyl radical and the prepolymer has crosslinkable double bonds; or
   (iii) the silane has polymerizable double bonds and the prepolymer has cross-linkable double bonds; or
   (iv) the silane has a mercapto group and the prepolymer has crosslinkable double bonds; or
   (v) the silane has a isocyanate group and the prepolymer is a polyol; or
   (vi) the silane has a hydroxyl group and the prepolymer is isocyanate; or
   (vii) the silane has an amino group and the prepolymer is epoxy resin.

33. The container of claim 32, wherein the hydrolytic condensate is a silane with an acrylic group and the prepolymer is acrylate.

34. The container of claim 1 where the internal surface comprises a PECVD tie coating or layer, a barrier coating or layer, and a pH protective coating or layer or one of the individual coatings or layers.

35. The container in claim 34 where the tie coating or layer is $SiO_xC_yH_z$ or $SiN_xC_yH_z$ in which x is from about 0.5 to about 2.4 as measured by X-ray photoelectron spectroscopy (XPS), y is from about 0.6 to about 3 as measured by XPS, and z is from about 2 to about 9 as measured by Rutherford backscattering spectrometry (RBS) or hydrogen forward scattering (HFS).

36. The container in claim 34 where the tie coating or layer has an outer surface facing the internal surface and the tie coating or layer has an interior surface.

* * * * *